(12) United States Patent
Geist

(10) Patent No.: US 10,709,578 B2
(45) Date of Patent: Jul. 14, 2020

(54) SURGICAL BIOLOGICS DELIVERY SYSTEM AND RELATED METHODS

(71) Applicant: INTEGRITY IMPLANTS INC., Palm Beach Gardens, FL (US)

(72) Inventor: Wyatt Geist, Jupiter, FL (US)

(73) Assignee: INTEGRITY IMPLANTS INC., Palm Beach Gardens, FL (US)

( * ) Notice: Subject to any disclaimer, the term of this patent is extended or adjusted under 35 U.S.C. 154(b) by 0 days.

(21) Appl. No.: 16/113,040

(22) Filed: Aug. 27, 2018

(65) Prior Publication Data

US 2019/0060085 A1    Feb. 28, 2019

Related U.S. Application Data

(60) Provisional application No. 62/550,557, filed on Aug. 25, 2017.

(51) Int. Cl.
*A61F 2/46*         (2006.01)
*A61B 17/88*        (2006.01)
(Continued)

(52) U.S. Cl.
CPC ........ *A61F 2/4601* (2013.01); *A61B 17/7061* (2013.01); *A61B 17/8805* (2013.01);
(Continued)

(58) Field of Classification Search
CPC .............. A61B 17/56; A61B 2017/564; A61B 17/7061; A61B 17/7094; A61B 17/7097;
(Continued)

(56) References Cited

U.S. PATENT DOCUMENTS 4,309,777 A    1/1982 Patil
4,733,665 A    3/1988 Palmaz
(Continued)

FOREIGN PATENT DOCUMENTS

CN    101909548    7/2014
EP    1011503    2/1998
(Continued)

OTHER PUBLICATIONS

U.S. Appl. No. 16/444,888, To—owned by applicant, filed Dec. 13, 2012.
(Continued)

*Primary Examiner* — Larry E Waggle, Jr.
(74) *Attorney, Agent, or Firm* — Brian S. Boyer; Syndicated Law, PC

(57) ABSTRACT

A system and methods for a safe and efficient distributing of bone graft material into an intervertebral disc space are provided. Systems are provided for receiving, removing, and replacing of preloaded load cartridges in a rapid and repeating manner. The systems can also be designed for rapidly delivering the biologics from a single load cartridge and, to even further facilitate a rapid and repeating delivery of biologics, the load cartridge and cartridge tamp can be adapted so that the cartridge tamp can capture and remove the load cartridge after delivery of fusion promoting material in the load cartridge.

20 Claims, 13 Drawing Sheets

(51) Int. Cl.
*A61F 2/44* (2006.01)
*A61F 2/28* (2006.01)
*A61B 17/70* (2006.01)
*A61F 2/30* (2006.01)
*A61B 17/56* (2006.01)

(52) U.S. Cl.
CPC ........ *A61B 17/8841* (2013.01); *A61F 2/2846* (2013.01); *A61F 2/442* (2013.01); *A61F 2/447* (2013.01); *A61F 2/4455* (2013.01); *A61F 2/4603* (2013.01); *A61F 2/4611* (2013.01); *A61B 2017/564* (2013.01); *A61F 2002/2835* (2013.01); *A61F 2002/305* (2013.01); *A61F 2002/30014* (2013.01); *A61F 2002/30019* (2013.01); *A61F 2002/3055* (2013.01); *A61F 2002/3093* (2013.01); *A61F 2002/30136* (2013.01); *A61F 2002/30177* (2013.01); *A61F 2002/30331* (2013.01); *A61F 2002/30476* (2013.01); *A61F 2002/30515* (2013.01); *A61F 2002/30545* (2013.01); *A61F 2002/30556* (2013.01); *A61F 2002/30565* (2013.01); *A61F 2002/30593* (2013.01); *A61F 2002/30677* (2013.01); *A61F 2002/30733* (2013.01); *A61F 2002/30904* (2013.01); *A61F 2002/4622* (2013.01); *A61F 2002/4631* (2013.01); *A61F 2002/4687* (2013.01)

(58) Field of Classification Search
CPC . A61B 17/88; A61B 17/8802; A61B 17/8805; A61B 17/8841; A61F 2002/2835; A61F 2/2846; A61F 2/442; A61F 2/4455; A61F 2002/4475; A61F 2/46; A61F 2/4601; A61F 2/4603; A61F 2/4611; A61F 2002/4631; A61F 2002/4687
See application file for complete search history.

(56) References Cited

U.S. PATENT DOCUMENTS

| | | | |
|---|---|---|---|
| 4,759,766 A | 7/1988 | Buettner-Janz et al. | |
| 4,820,305 A | 4/1989 | Harms et al. | |
| 4,997,432 A | 3/1991 | Keller | |
| 5,192,327 A | 3/1993 | Brantigan | |
| 5,221,261 A | 6/1993 | Termin et al. | |
| 5,609,635 A | 3/1997 | Michelson | |
| 5,658,336 A | 8/1997 | Pisharodi | |
| 5,976,187 A | 11/1999 | Richelsoph | |
| 5,980,522 A | 11/1999 | Koros | |
| 5,980,552 A | 11/1999 | Pinchasik et al. | |
| 6,039,761 A | 3/2000 | Li et al. | |
| 6,102,950 A | 8/2000 | Vaccaro | |
| 6,176,882 B1 | 1/2001 | Biedermann | |
| 6,193,757 B1 | 2/2001 | Foley et al. | |
| 6,368,351 B1 | 4/2002 | Glenn et al. | |
| 6,375,682 B1 | 4/2002 | Fleischmann et al. | |
| 6,395,031 B1 | 5/2002 | Foley et al. | |
| 6,409,766 B1 | 6/2002 | Brett | |
| 6,419,705 B1 | 7/2002 | Erickson | |
| 6,432,107 B1 | 8/2002 | Ferree | |
| 6,436,119 B1 | 8/2002 | Erb et al. | |
| 6,443,989 B1 | 9/2002 | Jackson | |
| 6,482,235 B1 | 11/2002 | Lambrecht et al. | |
| 6,488,710 B2 | 12/2002 | Besselink | |
| 6,575,899 B1 | 6/2003 | Foley et al. | |
| 6,582,439 B1 | 6/2003 | Sproul | |
| 6,582,441 B1 | 6/2003 | He et al. | |
| 6,582,467 B1 | 6/2003 | Teitelbaum | |
| 6,595,998 B2 | 7/2003 | Johnson et al. | |
| 6,620,169 B1 * | 9/2003 | Peterson | A61B 17/8833 606/93 |
| 6,666,891 B2 | 12/2003 | Boehm, Jr. et al. | |
| 6,821,276 B2 | 11/2004 | Lambrecht et al. | |
| 6,821,298 B1 | 11/2004 | Jackson | |
| 6,893,464 B2 | 5/2005 | Kiester | |
| 7,018,415 B1 | 3/2006 | McKay | |
| 7,083,650 B2 | 8/2006 | Moskowitz et al. | |
| 7,087,055 B2 | 8/2006 | Lim et al. | |
| 7,204,853 B2 | 4/2007 | Gordon et al. | |
| 7,214,243 B2 | 5/2007 | Taylor | |
| 7,217,293 B2 | 5/2007 | Branch | |
| 7,544,208 B1 | 6/2009 | Mueller et al. | |
| 7,621,950 B1 | 11/2009 | Globerman et al. | |
| 7,643,884 B2 | 1/2010 | Pond et al. | |
| 7,655,046 B2 | 2/2010 | Dryer et al. | |
| 7,678,148 B2 | 3/2010 | Peterman | |
| 7,731,751 B2 | 6/2010 | Butler et al. | |
| 7,771,473 B2 | 8/2010 | Thramann | |
| 7,819,921 B2 | 10/2010 | Grotz | |
| 7,828,845 B2 | 11/2010 | Estes et al. | |
| 7,828,849 B2 | 11/2010 | Lim | |
| 7,846,206 B2 | 12/2010 | Oglaza et al. | |
| 7,850,733 B2 | 12/2010 | Baynham et al. | |
| 7,862,618 B2 | 1/2011 | White et al. | |
| 7,879,098 B1 | 2/2011 | Simmons, Jr. | |
| 7,909,872 B2 | 3/2011 | Zipnick | |
| 7,918,888 B2 | 4/2011 | Hamada | |
| 8,062,375 B2 | 11/2011 | Glerum et al. | |
| 8,070,754 B2 | 12/2011 | Fabian et al. | |
| 8,070,813 B2 | 12/2011 | Grotz et al. | |
| 8,083,744 B2 | 12/2011 | Dorchak | |
| 8,088,163 B1 | 1/2012 | Kleiner | |
| 8,105,382 B2 | 1/2012 | Olmos et al. | |
| 8,110,004 B2 | 2/2012 | Valdevit et al. | |
| 8,118,813 B2 | 2/2012 | Perez-Cruet et al. | |
| 8,118,870 B2 | 2/2012 | Gordon et al. | |
| 8,123,810 B2 | 2/2012 | Gordon et al. | |
| 8,167,950 B2 | 5/2012 | Aferzon et al. | |
| 8,182,538 B2 | 5/2012 | O'Neil et al. | |
| 8,187,332 B2 | 5/2012 | McLuen | |
| 8,236,058 B2 | 8/2012 | Fabian et al. | |
| 8,241,363 B2 | 8/2012 | Sommerich et al. | |
| 8,246,572 B2 | 8/2012 | Cantor et al. | |
| 8,267,939 B2 | 9/2012 | Cipoletti et al. | |
| 8,353,961 B2 | 1/2013 | McClintock | |
| 8,353,963 B2 | 1/2013 | Glerum | |
| 8,425,612 B2 * | 4/2013 | Perez-Cruet | A61F 2/4611 606/249 |
| 8,491,659 B2 | 7/2013 | Weiman et al. | |
| 8,551,173 B2 | 10/2013 | Lechmann et al. | |
| 8,628,578 B2 | 1/2014 | Miller et al. | |
| 8,632,595 B2 | 1/2014 | Weiman | |
| 8,663,332 B1 | 3/2014 | To | |
| 8,845,731 B2 | 9/2014 | Weiman | |
| 8,852,279 B2 | 10/2014 | Weiman et al. | |
| 8,926,704 B2 | 1/2015 | Glerum et al. | |
| 8,936,641 B2 | 1/2015 | Cain | |
| 8,940,048 B2 | 1/2015 | Butler et al. | |
| 8,940,052 B2 | 1/2015 | Lechmann et al. | |
| 8,986,387 B1 | 3/2015 | To | |
| 9,034,041 B2 | 5/2015 | Wolters | |
| 9,039,771 B2 | 5/2015 | Glerum et al. | |
| 9,060,876 B1 | 6/2015 | To | |
| 9,138,328 B2 | 9/2015 | Butler et al. | |
| 9,186,193 B2 * | 11/2015 | Kleiner | A61B 17/8822 |
| 9,186,259 B2 | 11/2015 | To | |
| 9,216,095 B2 | 12/2015 | Glerum et al. | |
| 9,278,008 B2 | 3/2016 | Perloff et al. | |
| 9,320,610 B2 | 4/2016 | Alheidt et al. | |
| 9,333,092 B2 | 5/2016 | To | |
| 9,351,848 B2 | 5/2016 | Glerum et al. | |
| 9,402,733 B1 | 8/2016 | To | |
| 9,402,739 B2 | 8/2016 | Weiman et al. | |
| 9,445,918 B1 | 9/2016 | Lin et al. | |
| 9,463,052 B2 | 10/2016 | Geist | |
| 9,474,625 B2 | 10/2016 | Weiman | |
| 9,480,574 B2 | 11/2016 | Lee et al. | |
| 9,545,316 B2 | 1/2017 | Ashley et al. | |
| 9,561,116 B2 | 2/2017 | Weiman et al. | |
| 9,566,168 B2 | 2/2017 | Glerum et al. | |
| 9,655,744 B1 | 5/2017 | Pimenta | |

(56) References Cited

U.S. PATENT DOCUMENTS

| | | | |
|---|---|---|---|
| 9,675,469 B2 | 6/2017 | Landry et al. |
| 9,717,601 B2 | 8/2017 | Miller |
| 9,737,411 B2 | 8/2017 | Loebl et al. |
| 9,795,493 B1 | 10/2017 | Bannigan |
| 9,801,640 B2 | 10/2017 | O'Neil et al. |
| 9,801,733 B2 | 10/2017 | Wolters et al. |
| 9,801,734 B1 | 10/2017 | Stein et al. |
| 9,883,953 B1 | 2/2018 | To |
| 9,889,019 B2 | 2/2018 | Rogers et al. |
| 9,907,673 B2 | 3/2018 | Weiman et al. |
| 9,913,727 B2 | 3/2018 | Thommen et al. |
| 9,913,736 B2 | 3/2018 | To |
| 9,987,143 B2 | 6/2018 | Robinson et al. |
| 9,999,517 B2 | 6/2018 | To |
| 10,022,243 B2 * | 7/2018 | Emery | A61F 2/4601 |
| 10,058,350 B2 | 8/2018 | Geist |
| 10,080,592 B2 | 9/2018 | Geist |
| 10,085,849 B2 | 10/2018 | Weiman et al. |
| 10,098,757 B2 | 10/2018 | Logan et al. |
| 10,105,238 B2 | 10/2018 | Koch et al. |
| 10,143,569 B2 | 12/2018 | Weiman et al. |
| 10,149,773 B2 | 12/2018 | To |
| 10,154,911 B2 | 12/2018 | Predick et al. |
| 10,322,014 B2 | 6/2019 | To |
| 10,383,743 B2 | 8/2019 | To |
| 10,492,925 B2 * | 12/2019 | Hollister | A61F 2/4601 |
| 2002/0040243 A1 | 4/2002 | Attali |
| 2003/0074075 A1 | 4/2003 | Thomas et al. |
| 2003/0083746 A1 | 5/2003 | Kuslich |
| 2004/0010315 A1 | 1/2004 | Song |
| 2004/0024463 A1 | 2/2004 | Thomas et al. |
| 2005/0256576 A1 | 11/2005 | Moskowitz et al. |
| 2006/0100706 A1 | 5/2006 | Shadduck |
| 2006/0122701 A1 | 6/2006 | Kiester |
| 2006/0167547 A1 | 7/2006 | Suddaby |
| 2006/0287729 A1 | 12/2006 | Segal et al. |
| 2007/0118222 A1 | 5/2007 | Lang |
| 2007/0173939 A1 | 7/2007 | Kim et al. |
| 2007/0219634 A1 | 9/2007 | Greenhalgh |
| 2008/0009876 A1 | 1/2008 | Sankaran et al. |
| 2008/0021556 A1 | 1/2008 | Edie |
| 2008/0021559 A1 | 1/2008 | Thramann |
| 2008/0147193 A1 | 6/2008 | Matthis |
| 2008/0234687 A1 | 9/2008 | Schaller |
| 2008/0281346 A1 | 11/2008 | Greenhalgh |
| 2008/0281424 A1 | 11/2008 | Parry et al. |
| 2009/0018524 A1 | 1/2009 | Greenhalgh |
| 2009/0076607 A1 | 3/2009 | Aalsma et al. |
| 2009/0138083 A1 | 5/2009 | Biyani |
| 2009/0281551 A1 | 5/2009 | Frey |
| 2009/0222043 A1 | 9/2009 | Altarac |
| 2009/0234389 A1 | 9/2009 | Chuang |
| 2010/0010542 A1 | 1/2010 | Jackson |
| 2010/0010633 A1 | 1/2010 | Kohm |
| 2010/0042218 A1 | 2/2010 | Nebosky et al. |
| 2010/0198352 A1 | 8/2010 | Edie |
| 2010/0217325 A1 | 8/2010 | Hochschuler |
| 2010/0222884 A1 | 9/2010 | Greenhalgh |
| 2010/0234956 A1 | 9/2010 | Attia |
| 2010/0286783 A1 | 11/2010 | Lechmann et al. |
| 2010/0292796 A1 | 11/2010 | Greenhalgh |
| 2011/0022090 A1 | 1/2011 | Gordon |
| 2011/0029082 A1 | 2/2011 | Hall |
| 2011/0046748 A1 | 2/2011 | Martin |
| 2011/0130835 A1 | 6/2011 | Ashley |
| 2011/0172774 A1 | 7/2011 | Varela |
| 2011/0190816 A1 | 8/2011 | Sheffer |
| 2011/0282453 A1 | 11/2011 | Greenhalgh |
| 2011/0301712 A1 | 12/2011 | Palmatier |
| 2011/0319997 A1 | 12/2011 | Glerum |
| 2012/0029636 A1 | 2/2012 | Ragab |
| 2012/0035729 A1 | 2/2012 | Glerum et al. |
| 2012/0046748 A1 | 2/2012 | Weiman |
| 2012/0083889 A1 | 4/2012 | Purcell |
| 2012/0089185 A1 | 4/2012 | Gabelberger |
| 2012/0109319 A1 | 5/2012 | Perisic |
| 2014/0039625 A1 | 7/2012 | To |
| 2012/0209386 A1 | 8/2012 | Triplett et al. |
| 2012/0271396 A1 | 10/2012 | Zheng |
| 2012/0290090 A1 | 11/2012 | Glerum et al. |
| 2012/0303126 A1 | 11/2012 | Kirschman |
| 2013/0006365 A1 * | 1/2013 | Pepper | A61F 2/447 |
| | | | 623/17.16 |
| 2013/0023996 A1 | 1/2013 | McCormack |
| 2013/0184822 A1 | 7/2013 | Kleiner |
| 2014/0243981 A1 | 8/2014 | Davenport et al. |
| 2015/0100128 A1 | 4/2015 | Glerum et al. |
| 2015/0190242 A1 | 7/2015 | Blain et al. |
| 2015/0374508 A1 | 12/2015 | Sandul |
| 2016/0015530 A1 | 1/2016 | To |
| 2016/0256291 A1 | 9/2016 | Miller |
| 2016/0317315 A1 | 11/2016 | Weiman |
| 2016/0338854 A1 | 11/2016 | Serhan et al. |
| 2017/0119540 A1 | 5/2017 | Greenhalgh |
| 2017/0209282 A1 | 7/2017 | Aghayev et al. |
| 2017/0224504 A1 | 8/2017 | Butler et al. |
| 2017/0224505 A1 | 8/2017 | Butler et al. |
| 2017/0231780 A1 | 8/2017 | D'urso |
| 2017/0239063 A1 | 8/2017 | Predick |
| 2017/0281358 A1 | 10/2017 | Wagner et al. |
| 2017/0333198 A1 | 11/2017 | Robinson |
| 2017/0333203 A1 | 11/2017 | Glerum |
| 2017/0354512 A1 | 12/2017 | Weiman et al. |
| 2018/0042735 A1 | 2/2018 | Schell et al. |
| 2018/0193164 A1 | 7/2018 | Shoshtaev |
| 2018/0256357 A1 | 9/2018 | To |
| 2018/0296361 A1 | 10/2018 | Butler et al. |
| 2018/0360489 A1 | 12/2018 | Geist |
| 2019/0053913 A1 | 2/2019 | To |
| 2019/0117409 A1 | 4/2019 | Shoshtaev |
| 2019/0209339 A1 | 7/2019 | To |
| 2019/0254841 A1 | 8/2019 | To |
| 2019/0269521 A1 | 9/2019 | Shoshtaev |

FOREIGN PATENT DOCUMENTS

| | | |
|---|---|---|
| EP | 1233732 | 2/2001 |
| EP | 2327377 | 3/2002 |
| EP | 1532949 | 11/2003 |
| EP | 2237748 | 1/2009 |
| EP | 13862126 | 12/2013 |
| EP | 19162909.6 | 12/2013 |
| EP | 14842880 | 6/2016 |
| EP | 16740662 | 11/2017 |
| JP | 2009/505686 | 7/2005 |
| WO | WO 1996/040015 | 6/1996 |
| WO | WO 2000/044319 | 1/2000 |
| WO | WO 2001/066047 | 7/2001 |
| WO | WO 2008/005627 | 5/2007 |
| WO | WO 2007/076374 | 7/2007 |
| WO | WO 2008/035849 | 7/2007 |
| WO | WO 2008/033457 | 3/2008 |
| WO | WO 2008/089252 | 7/2008 |
| WO | WO 2008/121162 | 10/2008 |
| WO | WO 2010/077359 | 7/2010 |
| WO | WO 2012/135764 | 10/2012 |

OTHER PUBLICATIONS

U.S. Appl. No. 16/527,294, To—owned by applicant, filed Dec. 13, 2012.

U.S. Appl. No. 16/682,828, Shoshtaev—owned by applicant, filed Jan. 10, 2017.

U.S. Appl. No. 60/666,945, Bulter, et al., filed Mar. 31, 2005.

U.S. Appl. No. 61/585,724, Geist—owned by Applicant, filed Jan. 12, 2012.

U.S. Appl. No. 61/737,054, To—owned by Applicant, filed Dec. 15, 2013.

U.S. Appl. No. 61/875,688, To—owned by Applicant, filed Oct. 4, 2013.

U.S. Appl. No. 62/232,021 (priority for U.S. Pat. No. 10,058,350, cited herein), Geist—owned by Applicant, filed Sep. 24, 2015.

(56) References Cited

OTHER PUBLICATIONS

U.S. Appl. No. 62/444,663 (priority for U.S. 2018/0193164, cited herein), Shoshtaev—owned by Applicant, filed Jan. 10, 2017.
U.S. Appl. No. 62/471,206 (priority for U.S. 2018/0193164, cited herein), Shoshtaev—owned by Applicant, filed Jan. 10, 2017.
U.S. Appl. No. 62/481,565 (priority for U.S. 2018/0193164, cited herein), Shoshtaev—owned by Applicant, filed Jan. 10, 2017.
U.S. Appl. No. 62/536,335 (priority for PCT/US2018/43517, cited herein), To—owned by Applicant, filed Jul. 24, 2017.
U.S. Appl. No. 62/550,557 (priority for U.S. Appl. No. 16/113,040, cited herein), Geist—owned by Applicant, filed Aug. 25, 2017.
PCT/US2013/052799, To—owned by Applicant, Jul. 31, 2012.
Written opinion and search report for PCT/US2013/052799, To—owned by Applicant, Dec. 2, 2012.
PCT/US2013/073435 Published as WO 2014/093136, To—owned by Applicant, Dec. 5, 2013.
Written opinion and search report for PCT/US2013/073435, To—owned by Applicant, Apr. 30, 2012.
PCT/US2014/054437, To—owned by Applicant, Feb. 26, 2014.
Written opinion and search report for PCT/US2014/054437, To—owned by Applicant, Jan. 6, 2015.
PCT/US2016/014100, To—owned by Applicant, Dec. 17, 2015.
Written opinion and search report for PCT/US2016/014100, To—owned by Applicant, Jan. 6, 2015.
PCT/US2017/52708, To—owned by Applicant, Sep. 21, 2017.
Written opinion and search report for PCT/US2017/52708, To—owned by Applicant, Sep. 21, 2017.
PCT/US2016/053467 Published as WO 2017/053813, Geist—owned by Applicant, Sep. 24, 2015.
Written opinion and search report for PCT/US2016/053467, Geist—owned by Applicant, Sep. 24, 2015.
PCT/US2018/13207 Published as WO 2018/132502, Shoshtaev—owned by Applicant, Jan. 10, 2018.
Written opinion and search report for PCT/US2018/13207, Shoshtaev—owned by Applicant, Jan. 10, 2018.
PCT/US2018/43517, To—owned by Applicant, Jul. 24, 2018.
Written opinion and search report for PCT/US2018/43517, To—owned by Applicant, Jul. 24, 2018.
PCT/US2019/20354, Shoshtaev—owned by Applicant, Mar. 1, 2018.
Written opinion and search report for PCT/US2019/20354, Shoshtaev—owned by Applicant, Mar. 1, 2018.
Basho, R. et al. Lateral interbody fusion: Indications and techniques. Operative techniques in orthopaedics 21(3): 204-207 (Sep. 2011).
Caliber. www.globusmedical.com [online] URL: http://www.globusmedical.com/mis/166-caliber [retrieved on Jul. 27, 2012].
Cole, D. et al. Comparison of low back fusion techniques: transforaminal lumbar interbody fusio (TLIF) or posterior lumbar interbody fusion (PLIF) approaches. Curr rev Musculoskelet med 2(2): 118-126 published online Apr. 29, 2009 Doi: 1007/s12178-009-9053-B10 [retrieved Jun. 2009].
CAPSTONE® PEEK spinal system PLIF anf TLIF surgical technique. Medtronic Sofamor Danek 1-36 (2009).
COALIGN. Introducing AccuLIF expandable lumbar interbody fusion technology. [online] URL: http://www.coalign.com [retrieved on Jul. 27, 2012].
Chapman, C. A. Design of an expandable intervertebral cage utilizing shape memory alloys. University of Toledo and OhioLINK, 2011. [online] URL: http://etd.ohiolink.edu/view.cgi?acc_num=toledo1302226375 [retrieved Feb. 13, 2013].
Dorso-Lumbar Vertebral Body Cages DSC, Sintea Plustek. [online] URL: http://www.sinteaplustek.com/spine_dsc_eng.html [retrieved on Feb. 13, 2013].
"Integrity Implants" (Integrity Implants) URL: http://www.integrityimplants.com/ [retrieved from internet Sep. 17, 2018].
"Integrity Implants v3" (Integrity Implants) URL: https://vimeo.com/232697959 ; [retrieved from the internet Nov. 16, 2017].
Interbody Fusion Cage (Neo IC) Source, www.tradekorea.com [online] URL: http://www.tradekorea.com/product-detail/P00015150/Interbody_Fusion_Cage__Neo_IC_.html [retrieved Feb. 13, 2013].
Kaech, D.L. et al. Spinal restabilization procedures, diagnostic and therapeutic aspects of intervertebral fusion cages, artificial discs and mobile implants. Elsevier Science B.V. Part II: 121-204(2002).
Kiapour, A. et al. A biomechanical finite element study of subsidence and migration tendencies in stand-alone fusion procedures—comparison of an in situ expandable device with a rigid device. J Spine 1(4): 5 pages (2012).
Le Huec, J.C. et al. Endoscope surgery of the spine, a review of 4 years? Practice, maltrise orthopaedique. Jan. 1999 [online] URL: http://www.maitrise-orthop.com/viewPage_us.do?id=435 [retrieved on Feb. 5, 2013].
Powerbuilt. Powerbuilt 940378 medium tailpipe expander set. [online] URL: http://www.amazon.com/Powerbuilt-940377-Tailpipi-Expander-Series/dp/B004KED6A [retrieved on Feb. 17, 2013].
PR Newswire. Benvenue Medical starts enrolling patients in the post-market lift study on the luna interbody spacer system for degenerative disc disease. Mar. 20, 2012, [online] URL: http://www.prnewswire.com/news-releases/benvenue-medical-starts-enrolling-patients-in-the-post-market-lift-study-on-the-luna-interbody-spacer-system-for-degenerative-disc-disease-143441246.html [retrieved on Jan. 27, 2013].
Sasani, M. et al. Single-stage posterior corpectomy and expandable cage placement for treatment of thoracic or lumbar burst fractures. Spine 34(1): E33-E40 (Jan. 1, 2009).
Spineology. OptiMesh 1500E deploying grafting system. [online] URL: http://www.spineology.com/fb/intl/products/products/optimesh 1500e.html (retrieved Jun. 3, 2013).
STAXX XD, www.spinewave.com. [online] URL: http://www.spinewave.com/products/xd_us.html [retrieved on Jan. 27, 2013].
SynFix-LR System. Instruments and implants for stand-alone anterior lumbar interbody fusion (ALIF). Synthes SynFix-LR system technique guide 52 pages (2010).
Transforaminal Lumbar Interbody Fusion (TLIF). Virgina spine institute, Reston Virgina. [online] URL: http://www.spinemd.com/operative-treatments/tlif- transforaminal-lumbat-interbody-fusion.com 1-6 (2013). [retrieved on Jun. 16, 2013].
Uchida, K. et al. Anterior expandable strut cage replacement for osteoporotic thoracolumbar vertebral collapse. J Neurosurg Spine 4(6): 454-462 (Jun. 2006).
Xenos. Cage mesh system for spine. Biotek Chetan Meditech Pvt. Ltd. [online] URL: http://www.biotekortho.net/spine-treatment.html [retrieved on Feb. 13, 2013].
Zeus-O, [online] URL: http://www.amendia.com/zeuso.html [retrieved on Jan. 27, 2013].
PCT/US2011/049377 Published as WO 2012/027685, Saunders, et al., filed Aug. 26, 2011.

* cited by examiner

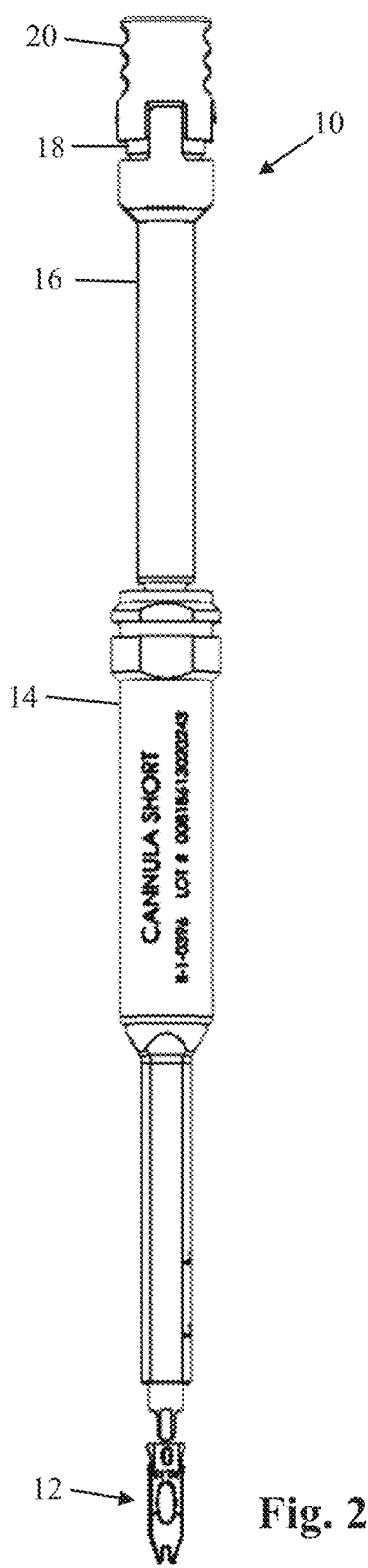
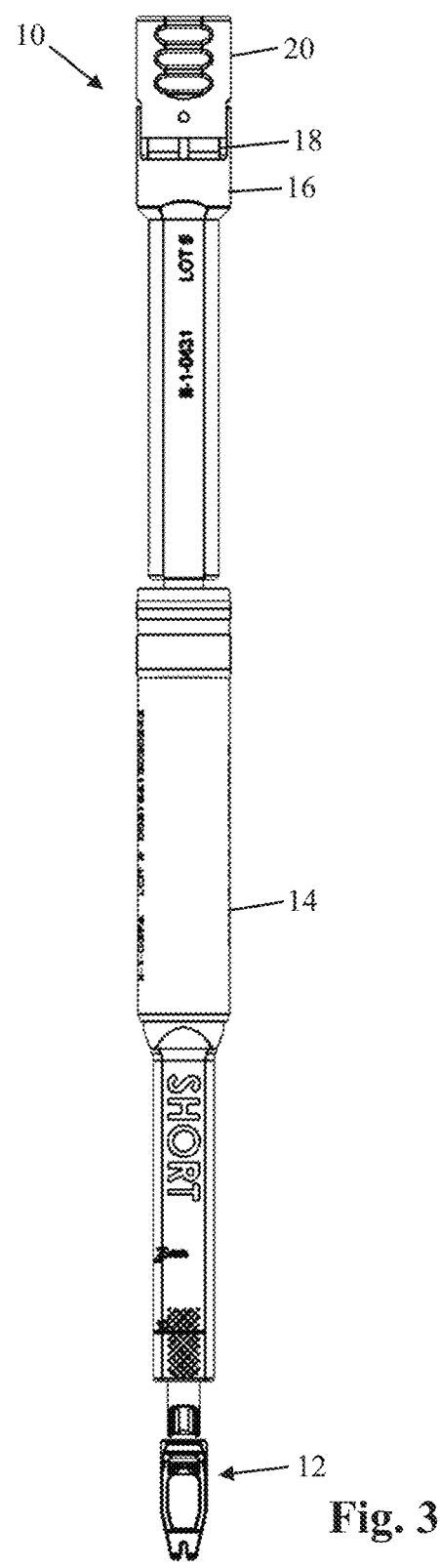
Fig. 2
Fig. 3

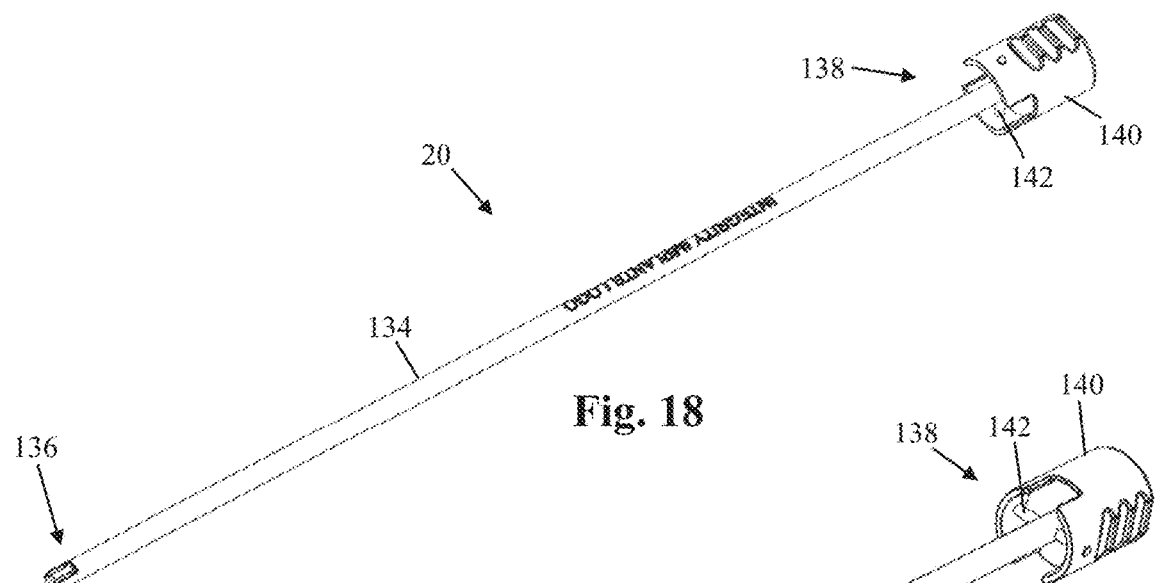
Fig. 18
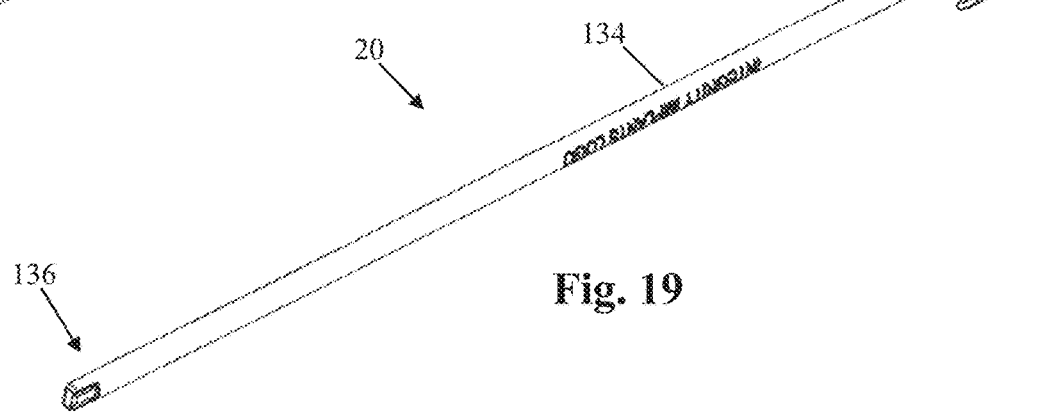
Fig. 19
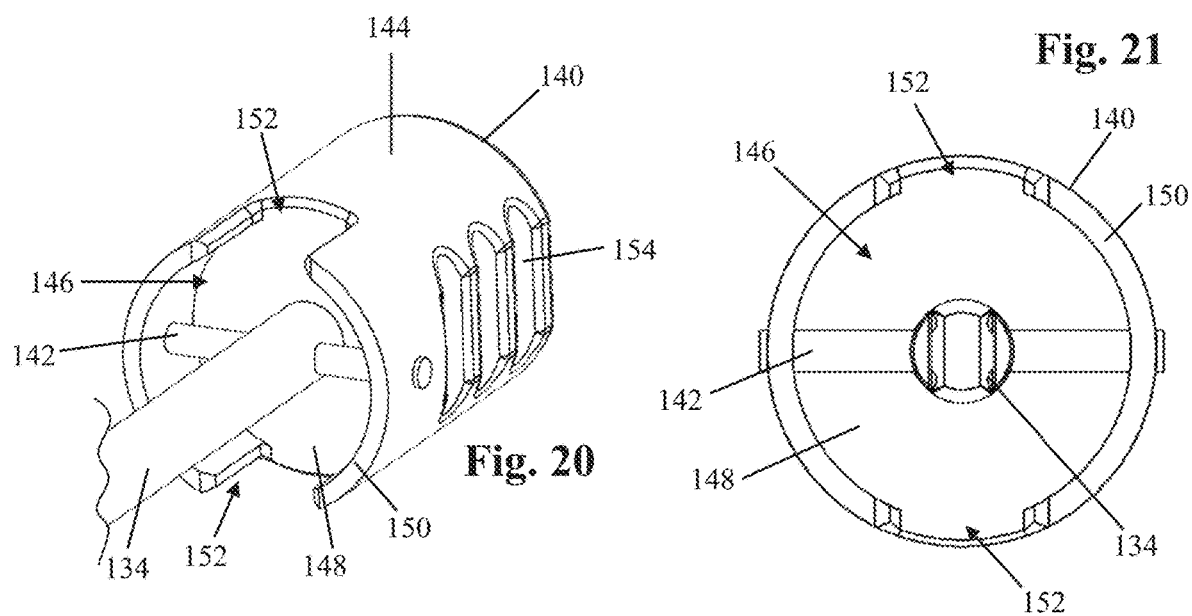
Fig. 20
Fig. 21

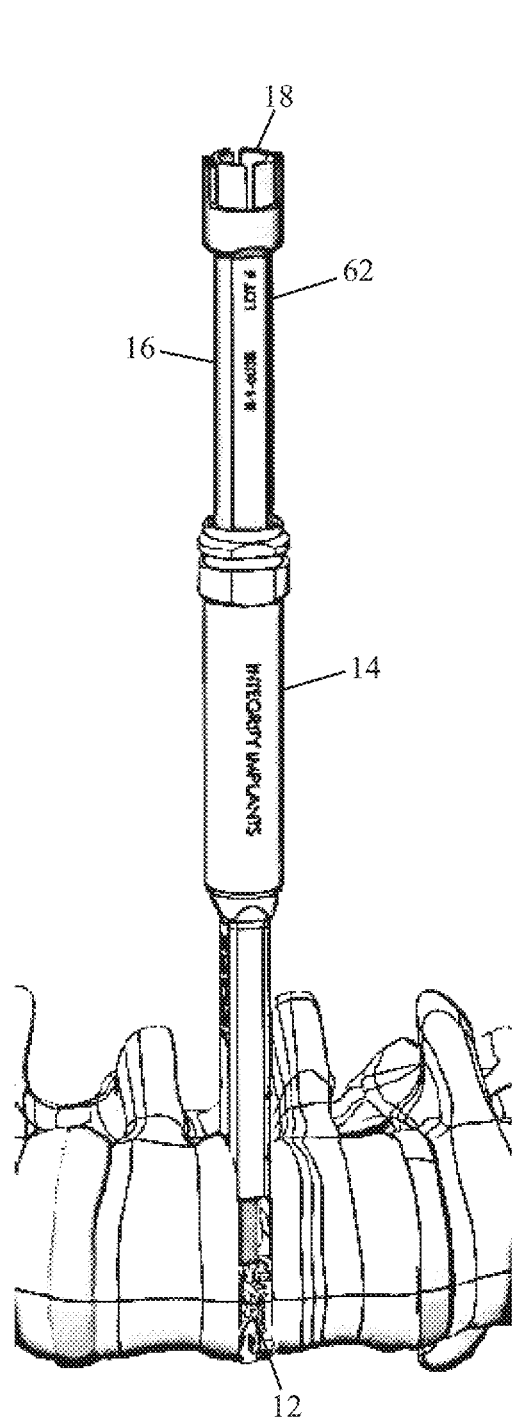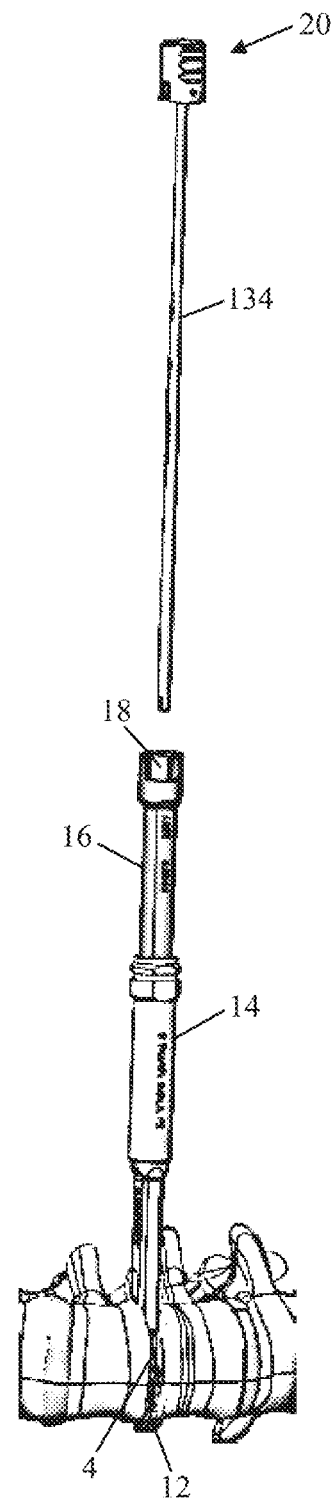
Fig. 29
Fig. 30

SURGICAL BIOLOGICS DELIVERY SYSTEM AND RELATED METHODS

CROSS-REFERENCE TO RELATED APPLICATIONS

This application claims the benefit of U.S. Provisional Application No. 62/550,557, filed Aug. 25, 2017, which is hereby incorporated by reference herein in it's entirety.

BACKGROUND

Field of the Invention

The teachings provided herein are directed to systems and methods for distributing bone graft material into an intervertebral disc space.

Description of the Related Art

Bone grafts are used in spinal fusion to stabilize the vertebrae, with a goal of creating a solid bridge of bone between two or more vertebrae. The fusion process includes "arthrodesis", which can be thought of as the mending or welding together of two bones in a spinal joint space. Spinal fusion may be recommended for a variety of conditions that might include, for example, a spondylolisthesis, a degenerative disc disease, a recurrent disc herniation, or perhaps to correct a prior surgery.

A fusion cage can be inserted with bone graft material to help support the disc space during the fusion process. In fact, fusion cages are frequently used in such procedures to support and stabilize the disc space until bone graft unites the bone of the opposing vertebral endplates in the disc space. A transforaminal lumbar interbody fusion (TLIF), for example, involves placement of posterior instrumentation (screws and rods) into the spine, and the fusion cage loaded with bone graft can be inserted into the disc space. Bone graft material can be pre-packed in the disc space or packed after the cage is inserted. TLIF can be used to facilitate stability in the front and back parts of the lumbar spine promoting interbody fusion in the anterior portion of the spine. Fusion in this region can be beneficial, because the anterior interbody space includes an increased area for bone to heal, as well as to handle increased forces that are distributed through this area. Traditionally, surgeons use a metal funnel and tamp to place bone graft, however, and this continues to add problems in the process. Other methods have been developed to address some of the problems, but problems still remain for the surgeon to manage. Ease of operation, procedural time, and safety, are focal points for improvements.

A common problem in spinal fusion is that the intervertebral space needs to be stabilized after the core of the disc is removed. Since the emptied disc space is often larger than the size of the access corridor, and since the fusion implants are typically smaller than the intervertebral disc space, there is a problem with reaching a long-term stability due to the mechanics and forces involved in the intervertebral space.

Existing spinal fusion implants are either made of a polymer such as Polyether Ether Ketone (PEEK), metal such as titanium, or ceramic such as silicon nitride. Some are made by a combination thereof. In any event, these materials are inert with respect to promoting osteogenesis. Some implants are made of PEEK coated with metal particles such as titanium or silver based due to the belief that the metal coatings are more osteogenic. However, the coatings can slough off from shear during implantation, or while in vivo, and can cause adverse reactions. Fusion promoting material can help increase the stability of the implant in the intervertebral space and encourage bone growth or fusion across the affected disc space.

Moreover, introducing biologics to the disc space in a safe, efficient, and reproducible manner is desired. As current methods can include, for example, the use of one or a combination of a bone funnel, syringe, and/or cannula, a manual mixing and packing of a fusion promoting material can be a required part of the process, and this increases the complexity of the process, lowers the ease of operation, and increases the procedural time required. Fusion-promoting material, or "biologics", by way of example, may include biologic bone, artificial bone matrix, collagen, protein, and the like. These materials can be referred to as an allograft, autograft, xenograft, or synthetic bone graft material, for example. The premixing of graft material can include use of a plasma concentrate, blood, bone marrow, platelet rich plasma, intravenous fluids, and can add significantly to procedural time, as it is done repeatedly during current procedures. Moreover, a bone tamp can be used as a plunger, for example, to repeatedly push the fusion promoting material into an intervertebral space through a cannula. One of skill will understand that it is not always a simple task to move such materials in to the intervertebral space easily, quickly, and safely. As such, with the complexity of the current delivery systems, and the numerous steps involved, the art will benefit from a system that is easy for the surgeon to handle, and that can deliver a desired amount of biologics quickly and safely, requiring less steps, less cumbersome handling of system parts, and less time, in the process.

One of skill in the art will recognize the problems addressed by the teachings herein and, namely, will appreciate having a fast and efficient system and method of introducing fusion promoting material that (i) is easier to operate during administration of a fusion promoting material into a subject; (ii) requires less procedural time to administer a desired amount of the fusion promoting material into the subject; and (iii) is safer to use during the administration procedure.

BRIEF DESCRIPTION OF THE DRAWINGS

Many advantages of the present disclosure will be apparent to those skilled in the art with a reading of this specification in conjunction with the attached drawings, wherein like reference numerals are applied to like elements and wherein:

FIG. 2 is a plan view of the surgical biologics delivery system of FIG. 1;

FIG. 3 is another plan view of the surgical biologics delivery system of FIG. 1, rotated 90° relative to the view of FIG. 2;

FIG. 18 is a perspective view of an example of a tamp forming part of the surgical biologics delivery system of FIG. 1;

FIG. 19 is another perspective view of the tamp of FIG. 18;

FIG. 20 is an enlarged perspective view of the proximal end of the tamp of FIG. 18;

FIG. 21 is an enlarged plan view of the proximal end of the tamp of FIG. 18;

FIG. 29 is a perspective view of another step of an example method of using the surgical biologics delivery system of FIG. 1 according to one embodiment of the disclosure, comprising a step of inserting a load cartridge of FIG. 15 into the inner cannula of FIG. 11;

FIG. 30 is a perspective view of another step of an example method of using the surgical biologics delivery system of FIG. 1 according to one embodiment of the disclosure, comprising a step of advancing a tamp of FIG. 18 into the load cartridge of FIG. 15;

SUMMARY

Figure 1:
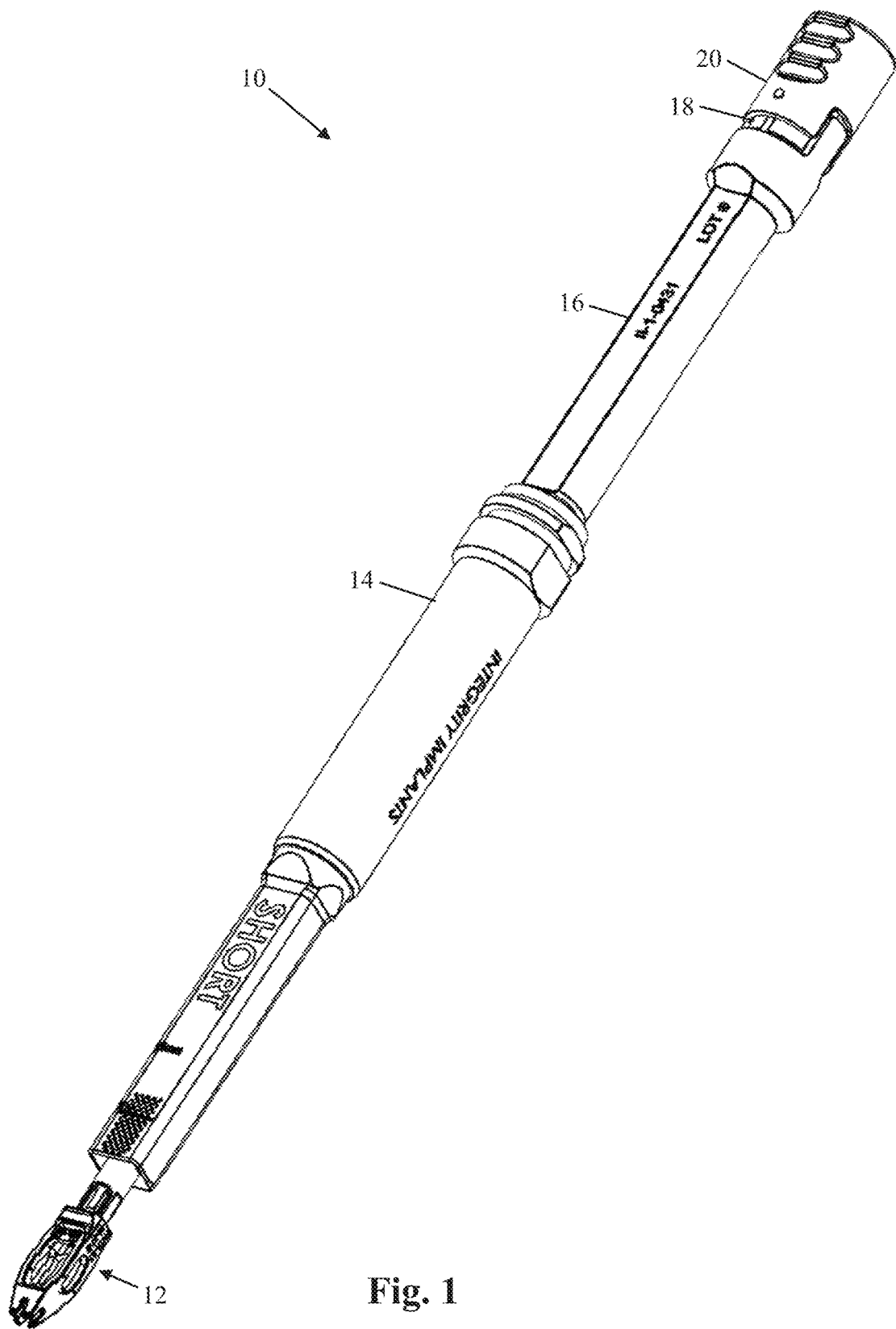
FIG. 1 is a perspective view of an example of a surgical biologics delivery system according to one embodiment of the disclosure
Figure 4:
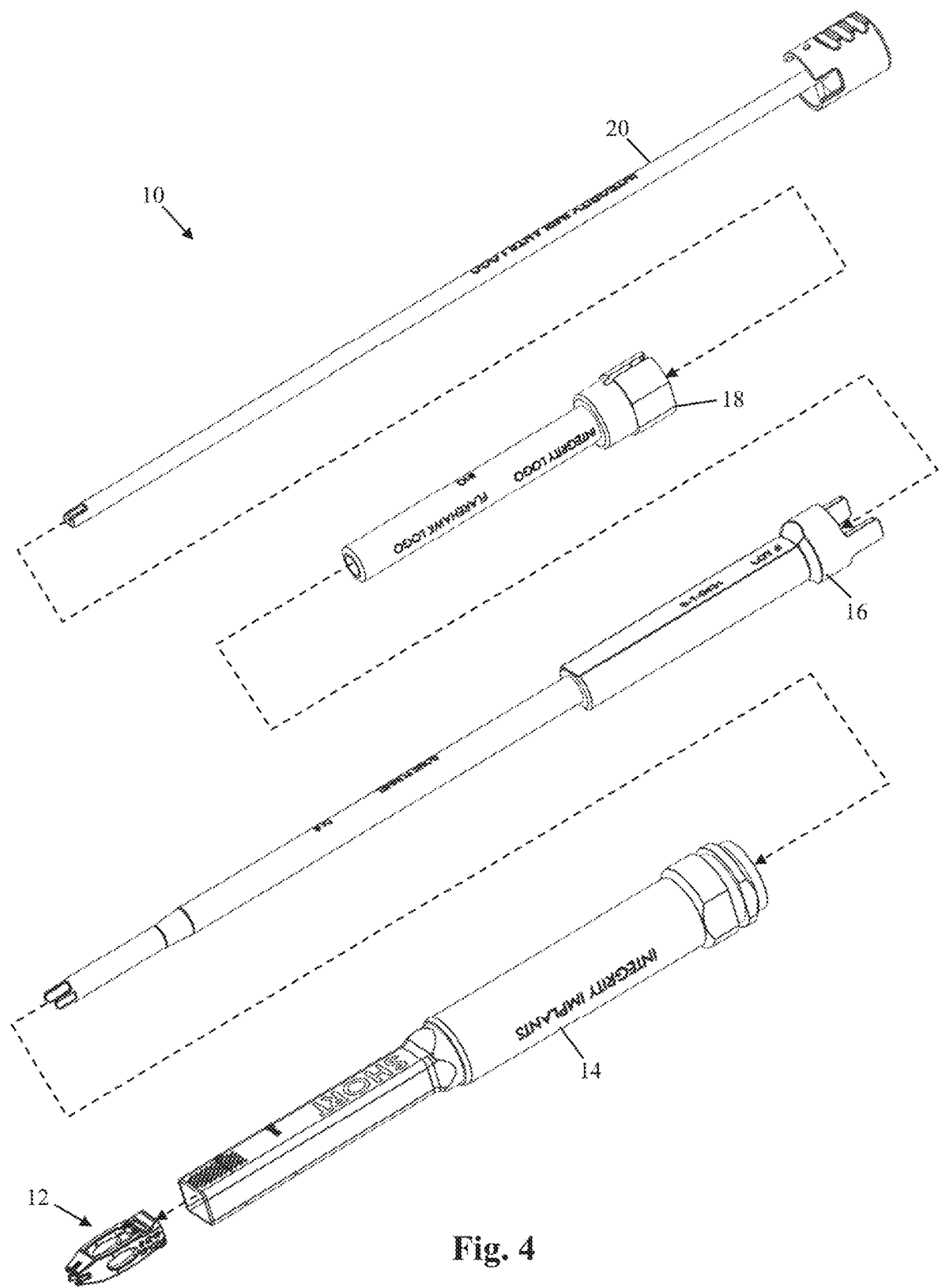
FIG. 4 is an exploded perspective view of the surgical biologics delivery system of FIG. 1.

A system and methods for a safe and efficient distributing of bone graft material into an intervertebral disc space are provided. In some embodiments, the teachings are directed to a biologics delivery system, comprising a cannula adapted for receiving a preloaded load cartridge and a cartridge tamp. The teachings are directed to a system for receiving, removing, and replacing of preloaded load cartridges in a rapid and repeating manner. This is further facilitated by a system that can also rapidly deliver the biologics from a single load cartridge. In some embodiments, to even further facilitate a rapid and repeating delivery of biologics, the load cartridge and cartridge tamp can be adapted so that the cartridge tamp can capture and remove the load cartridge after delivery of fusion promoting material in the load cartridge.

All of the systems taught herein provide safer and more efficient removal of load cartridges, faster and safer than any other state-of-the-art system. In some embodiments, the biologics delivery system comprises a cannula having a proximal portion, a proximal end, a distal portion, a distal end, and an engagement feature to engage a spinal implant; the proximal portion having a proximal lumen with a first inner diameter, and the distal portion having a distal lumen with a second inner diameter; wherein, the cannula is adapted for receiving a load cartridge in the proximal lumen of the cannula, the load cartridge having a proximal portion, a first removal component, an elongated shaft, and a lumen. In some embodiments, there is no first removal component.

In some embodiments, the cartridge tamp can have an elongated shaft and a second removal component. In such embodiments, the proximal lumen of the cannula can be configured to open into the distal lumen of the cannula, and the lumen of the load cartridge can be configured to open into the distal lumen of the cannula. The proximal lumen of the cannula can be adapted to receive the elongated shaft of the load cartridge, and the distal lumen of the cannula can be adapted to receive the elongated shaft of the load cartridge. In fact, the proximal portion of the load cartridge can be adapted to receive the elongated shaft of the cartridge tamp; and, the second removal component of the cartridge tamp can be adapted to (i) releasably connect with the first removal component and (ii) capture the load cartridge from the cannula when removing the cartridge tamp from the system. In some embodiments, the biologics system can further comprise the load cartridge. In some embodiments, there is no first removal component or second removal component.

It should be appreciated that, in some embodiments, the first removal component can be adapted to releasably engage with the second removal component using a friction fit connection between the first removal component and the second removal component. In some embodiments, the first removal component can be adapted to releasably engage with the second removal component using a snap fit connection between the first removal component and the second removal component. In some embodiments, the first removal component is adapted to releasably engage with the second removal component using a thread fit connection between the first removal component and the second removal component. And, in some embodiments, the first removal component can be adapted to releasably engage with the second removal component using a key and slot coupling connection between the first removal component and the second removal component. In fact, any connection known to one of skill in the art can be used to connect the first and second components. In some embodiments, for example, the first removal component and second removal component connect using a magnetic connection. The connection between the first and second component provides a safe and efficient way for the surgeon to "capture" a spent load cartridge and replace it with an additional load cartridge, quickly, to deliver a desired amount of fusion promoting material in vivo.

In some embodiments, the proximal end of the cannula can be further adapted to include a first indicator; and, likewise, the proximal portion of the load cartridge can be further adapted to include a second indicator complementary to the first indicator. In such embodiments, an assembly of the cannula and load cartridge can releasably fix the rotational position of the first removal component relative to the rotational position of the cannula to stop undesirable rotation between the cannula and load cartridge while holding the cannula in vivo to make the releasable connection between the first removal component and second removal component.

In some embodiments, the proximal end of the cartridge tamp can be further adapted to include a third indicator that is complementary to the assembly of the first and second indicators, such that the third indicator guides the cartridge tamp into the releasably-fixed assembly of the cannula and the load cartridge while making the releasable connection in vivo between the first removal component and second removal component.

In some embodiments, the first indicator can be configured to include a first prong extending proximally from the proximal end of the cannula and having a flat interior surface; the second indicator, likewise, can be configured with a outer-facing flat surface on the proximal portion of the load cartridge that is at least substantially complementary with the flat interior surface of the first prong; and, the cartridge tamp can further include a proximal cap having a recess as the third indicator, the recess being at least substantially complementary to the first prong.

The alignment between the first and second indicators, and first, second, and third indicators, provides a safe and efficient way for the surgeon to align the system components to quickly capture a spent load cartridge and replace it with an additional load cartridge, quickly, to deliver a desired amount of fusion promoting material in vivo.

As such, an advancement in load cartridges is also provided herein. The preloaded cartridges can be designed to have any bore size, but they are particularly valuable in that they include a large bore size, never before available, to enable one of skill to deliver the biologics into the disc space safely, and faster, than current state-of-the-art systems. As such, the load cartridges are designed as "repeater cartridges", with a configuration that delivers the fusion promoting material surprisingly quickly, and this is even further enhanced through additional quick-change features. The teachings are also directed to a method of delivering biologics into an intervertebral disc space of a subject. In some embodiments, the methods can include placing a cannula into the intervertebral disc space, the cannula adapted for receiving a preloaded load cartridge, preloaded with fusion promoting material; and, delivering the fusion promoting material by pushing a cartridge tamp into the preloaded cartridge to apply pressure that forces the fusion promoting material into the intervertebral disc space.

In some embodiments, the methods can include placing the cannula into the intervertebral disc space; inserting the load cartridge into the cannula, the load cartridge preloaded with fusion promoting material; and, delivering the fusion promoting material into the intervertebral disc space. In such embodiments, the delivering can include inserting the cartridge tamp into the load cartridge and pushing the fusion promoting material into the intervertebral disc space with the cartridge tamp to create a first empty load cartridge; removing the first empty load cartridge; inserting an additional load cartridge into the cannula, the additional load cartridge preloaded with additional fusion promoting material; pushing the additional fusion promoting material into the intervertebral disc space with the cartridge tamp to create an additional empty load cartridge; removing the additional empty load cartridge; and, repeating the inserting of the additional load cartridge, the pushing of the additional load cartridge, and removing of the additional load cartridge until a desired amount of fusion promoting material has been delivered to the intervertebral space. In some embodiments, the load cartridges are administered in series, where the first cartridge is "load cartridge 1", and each additional load cartridges, n, is an "n+1"$^{th}$ load cartridge, for example, where n can range from, perhaps, from 1 to 10.

In some embodiments, the methods can further comprise inserting a spinal implant into the intervertebral disc space. And, in some embodiments, the methods can further comprise docking the distal end of the cannula to the spinal implant.

Moreover, in some embodiments, the removing of the first load cartridge and the additional load cartridge can include releasably engaging the first removal component with the second removal component using a friction fit connection between the first removal component and the second removal component. And, in some embodiments, the removing of the first load cartridge and the additional load cartridge can include releasably engaging the first removal component with the second removal component using a snap fit connection between the first removal component and the second removal component. And, in some embodiments, the removing of the first load cartridge and the additional load cartridge can include releasably engaging the first removal component with the second removal component using a thread fit connection between the first removal component and the second removal component. And, in some embodiments, the removing of the first load cartridge and the additional load cartridge can include releasably engaging the first removal component with the second removal component using a key and slot coupling connection between the first removal component and the second removal component.

In some embodiments, the methods further include inserting an expandable shell into the intervertebral disc space. In some embodiments, the methods further include inserting a shim into the intervertebral disc space. In some embodiments, the methods further include inserting an expandable shell into the intervertebral disc space and inserting a shim into the expandable shell. And, in some embodiments, the methods further include expanding the expandable shell laterovertically.

It should be appreciated that, with regard to the systems and methods above that, in some embodiments, the key can be a pin, a bead, or any protuberance known to one of skill in the art, for example; and, the slot can be any configuration that facilitates a rapid and releasable capture with the key, including an open slot, a closed slot, an open dimple, a closed dimple, and the like. For example, a slot may be continuous in dimension or tapered for a friction fit, stepped to narrow for a tightening friction fit, stepped to narrow and then wide for a snap fit, and the like or any combination thereof. A thread connection can be any threaded connection and can include a friction fit, for example.

DETAILED DESCRIPTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The surgical biologics delivery system and related methods disclosed herein boasts a variety of inventive features and components that warrant patent protection, both individually and in combination.

In some embodiments, the biologics delivery system can comprise a cannula adapted for receiving a preloaded load cartridge and a cartridge tamp. In some embodiments, to further facilitate a rapid and repeating delivery of biologics, the load cartridge and cartridge tamp can be adapted so that the cartridge tamp can capture and remove the load cartridge after delivery of fusion promoting material in the load cartridge. The systems are designed for receiving, removing, and replacing of preloaded load cartridges in a rapid and repeating manner. This is further facilitated by systems that can also rapidly deliver the biologics from a single load cartridge. In some embodiments, to even further facilitate a rapid and repeating delivery of biologics, the load cartridge and cartridge tamp can be adapted so that the cartridge tamp can capture and remove the load cartridge after delivery of fusion promoting material in the load cartridge. It should be appreciated that the terms "biologics", "bone graft", "graft", "graft material", and "fusion promoting material" can be used interchangeably, in some embodiments. Materials which may be placed or injected into the intevertebral space include solid or semi-solid grafting materials, bone from removed from patient's facet, an iliac crest harvest from the patient, and bone graft extenders such as hydroxyapatite, demineralized bone matrix, and bone morphogenic protein. Examples of solid or semi-solid grafting material components include solid fibrous collagen or other suitable hard hydrophilic biocompatible material. Some materials may also include swelling for further vertical expansion of the intervertebral disc space.

As such, it should be appreciate that there is an advancement in load cartridges is provided herein, in addition to the advancement in the systems as a whole. The preloaded cartridges can be designed to have any bore size, but they are particularly valuable in that they include a large bore size, never before available, to enable one of skill to deliver the biologics into the disc space safely, and faster, than current state-of-the-art systems. As such, the load cartridges are designed as "repeater cartridges", with a configuration that delivers the fusion promoting material surprisingly quickly. As with the cannulas taught herein, although the bore size can range from about 1.0 mm to about 10.0 mm in diameter, for example, the bore is no less than 5.0 mm in diameter in some embodiments, and any range therein in increments of 1.0 mm. In some embodiments, however, the bore size can range from about 5.0 mm to about 10.0 mm in diameter, or from about 5.0 mm to about 6.0 mm in diameter, and any range therein in increments of 1.0 mm. In some embodiments, the bore size can be no less in diameter than about 5.0 mm, about 6.0 mm, about 7.0 mm, about 8.0 mm, about 9.0 mm, about 10.0 mm, and any amount therein in increments of 1.0 mm. In some embodiments, the bore size can be asymmetrical in dimensions, such that the height of the bore may not be equal to the width of the bore. For example, in some embodiments, the bore size ranges from 5.0 mm to 6.00 mm in height, and from 9.0 mm to 16.00 mm in width. And in some embodiments, the bore size ranges from 5.0 mm to 15.00 mm in height, and from about 9.0-15.0 mm in width. In some embodiments, "height" can refer to the craniocaudal direction of the bore, and "width" is the transverse direction with respect to the anatomical position. Of course, the outer diameter of the elongated shaft of the cartridge tamp is complementary to these dimensions for delivery of the fusion promoting material. In addition, the combination of the load cartridge and cartridge tamp provide a "capture" mechanism, as set-forth herein, in some embodiments.

Moreover, it should be appreciated that fusion-promoting material, or "biologics", by way of example, may include biologic bone, artificial bone matrix, collagen, protein, and the like, and these materials can be referred to as an allograft, autograft, xenograft, or synthetic bone graft material, for example. The premixing of graft material can include use of a plasma concentrate, blood, bone marrow, platelet rich plasma, intravenous fluids, and can add significantly to procedural time, as it is done repeatedly during current procedures.

In graft materials that have particles, in some embodiments, the particles can range in size from about 0.5 mm to about 5.0 mm in maximum dimension, about 0.5 mm to 5.0 mm in mean particle dimension, or about 0.5 mm to 5.0 mm in average particle dimension, across the particular population in the load cartridge. In some embodiments, the particles can range in size from about 1.0 mm to about 3.0 mm in maximum dimension, about 1.0 mm to about 3.0 mm in mean particle dimension, or about 1.0 mm to about 3.0 mm in average particle dimension, across the particular population in the load cartridge, and these dimensions can vary in increments of 0.1 mm across the range, in some embodiments.

The load cartridges can have a variety of volumes. In some embodiments, the load cartridge has a volume capacity for bone graft material in a range from about 0.5 ml to about 20 ml. In some embodiments, the load cartridge has a volume capacity for bone graft material in a range from about 0.75 ml to about 15 ml. In some embodiments, the load cartridge has a volume capacity for bone graft material in a range from about 1.0 ml to about 10 ml. In some embodiments, the load cartridge has a volume capacity for bone graft material in a range from about 1.5 ml to about 5.0 ml. And, in some embodiments, the load cartridge has a volume capacity for bone graft material of about 0.5 ml, about 1.0 ml, about 1.5 ml, about 2.5 ml, about 3.0 ml, about 3.5 ml, about 4.0 ml, about 4.5 ml, about 5.0 ml, about 5.5 ml, about 6.0 ml, about 6.5 ml, about 7.0 ml, about 7.5 ml, about 8.0 ml, about 8.5 ml, about 9.0 ml, about 9.5 ml, about 10.0 ml, about 11.0 ml, about 12.0 ml, about 13.0 ml, about 14.0 ml, about 15.0 ml, or about 20 ml, and amounts or ranges therein in increments of 0.1 ml.

The terms "system" and "kit" can also be used interchangeably, in some embodiments. In some embodiments, for example, a kit can include one or more repeater cartridges and a cartridge tamp. In some embodiments, a kit can include one or more repeater cartridges, a cartridge tamp, and a cannula for delivering biologics. In some embodiments, a kit can include one or more repeater cartridges, a cartridge tamp, a cannula for delivering biologics, and an outer cannula for receiving the cannula for delivering biologics. In some embodiments, a kit can include one or more repeater cartridges, a cartridge tamp, a cannula for delivering biologics, and an outer cannula for delivering a spinal implant and receiving the cannula for delivering biologics. In some embodiments, a kit can include one or more repeater cartridges, a cartridge tamp, a cannula for delivering biologics, an outer cannula for delivering a spinal implant and receiving the cannula for delivering biologics, and a spinal implant. And, in some embodiments, a kit will include a laterovertically expanding spinal implant and shim as described herein by reference in at least PCT Application No. PCT/US18/43517, filed Jul. 24, 2018, which is hereby incorporated by reference herein in its entirety. Instructions for using each kit can be included.

FIGS. 1-4 illustrate an example of a surgical biologics delivery system 10 according to some embodiments. The surgical biologics delivery system may be used in a variety of orthopedic applications. For the purpose of illustration, the surgical biologics delivery system 10 is described herein by example as being configured for use with a spinal implant 12 during a spinal fusion surgery. The example surgical biologics delivery system 10 described herein includes an outer cannula 14, an inner cannula 16, a load cartridge 18, and a tamp 20. Generally, the outer cannula 14 defines the surgical access corridor from the sterile operative field to the surgical target site within the patient, in this case (by way of example) an intervertebral disc space. As such, the outer cannula 14 is sized and configured to allow passage of a variety of surgical instruments to access and prepare the target disc space as well as facilitate insertion of the spinal implant 12 and further receive the inner cannula 16 therein. The inner cannula 16 is sized and configured to extend through the outer cannula 14 to facilitate introduction of biologics into the spinal implant 12. The inner cannula 16 is also configured to receive the load cartridge 18, which is loaded with the biologics to be inserted into the disc space. The tamp 20 is sized and configured to extend through the load cartridge 18 and inner cannula 16 to forcibly move the biologics from the load cartridge 18 through the inner cannula 16 and into the spinal implant 12.

It should be appreciated that the total length of the system is designed to facilitate delivery of the biologics in a surgical setting. For example, the total length of the system can range from about 70.0 mm to about 350.0 mm, from about 80.0 mm to about 300.0 mm, from about 90.0 mm to about 250.0 mm, from about 100.0 mm to about 200.0 mm, or any range or amount therein in increments of 1.0 mm.

Figure 5:
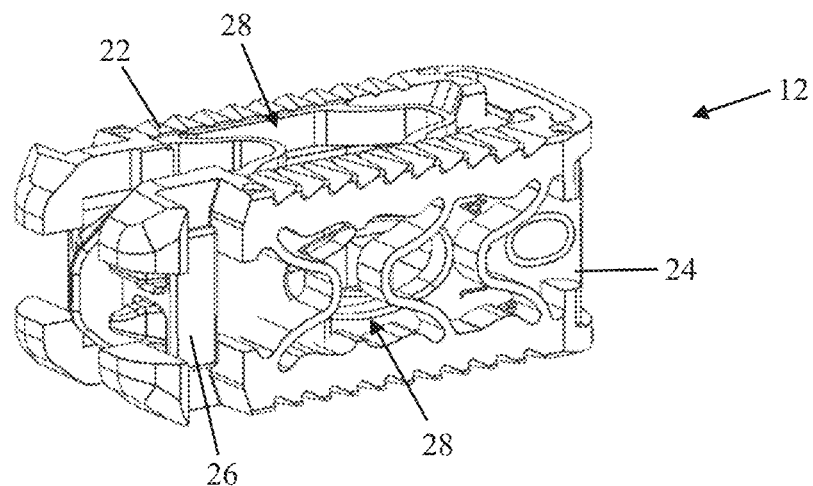
FIG. 5 is a perspective view of one example of a spinal implant suitable for use with the surgical biologics delivery system of FIG. 1.
Figure 6:
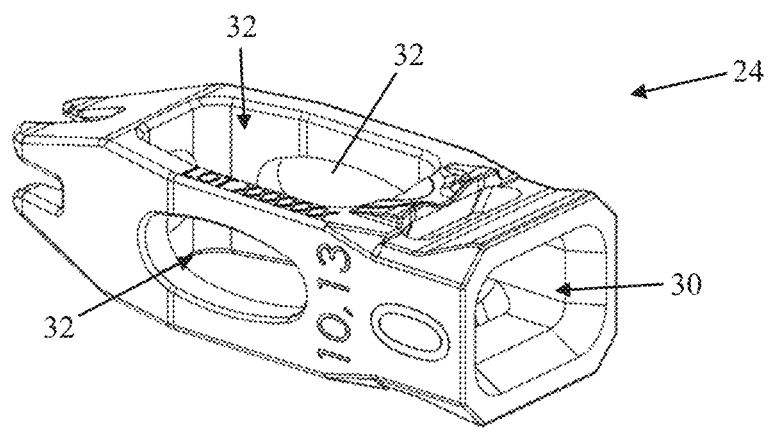
FIG. 6 is a perspective view of a shim forming part of the spinal implant of FIG. 5.
Figure 7:
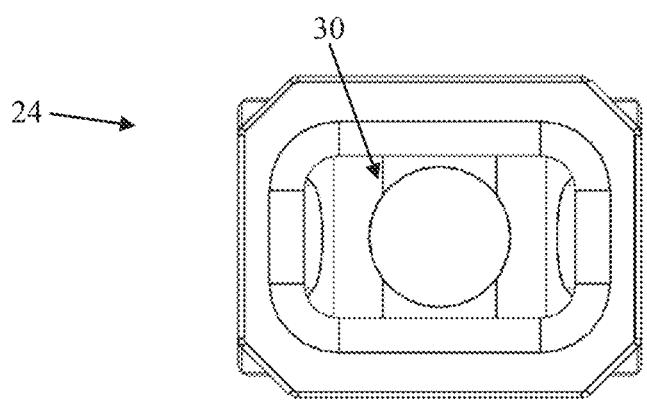
FIG. 7 is a rear plan view of the shim of FIG. 6.

The surgical biologics delivery system 10 of the present disclosure is suitable for use with a variety of spinal implants. For the purpose of illustration, FIGS. 5-7 depict one example of a spinal implant 12 suitable for use with the surgical biologics delivery system 10 described herein, according to some embodiments. By way of example, the spinal implant 12 may be one of the implants shown and described in commonly owned and PCT Application No. PCT/US18/43517, filed Jul. 24, 2018, the complete disclosure of which is incorporated by reference into this disclosure as if set-forth fully herein. The spinal implant 12 of the present example includes an expandable shell 22, shim 24, and guide element 26. The shell 22 is sized and configured for insertion into the target disc space through the outer cannula 14 in a collapsed state and thereafter expanded within the disc space by insertion of the shim 24 into the shell 22. Thus, the shim 24 is also sized and configured for insertion through the outer cannula 14. The collapsed shell 22 has a generally rectangular shape, including a generally rectangular lateral cross-sectional shape, which as will be explained below allows for efficient passage through the outer cannula 14. The shell 22 further includes a plurality of graft windows 28 positioned on each face of the generally rectangular shell 22 to allow for seepage of biologics to facilitate osteogenesis through the implant 12. The shim 24 includes a distal aperture 30 and a plurality of graft windows 32 positioned on each face of the generally rectangular shim 24. The distal aperture 30 is sized and configured to receive the distal end of the inner cannula therein to enable application of the biologics to the implant. In the instant example, the distal aperture 30 has a generally rectangular perimeter having a width dimension (e.g. the long edge of the rectangle) and height dimension (e.g. the short edge of the rectangle), however other shapes are possible. The graft windows 32 of the shim allow for seepage of biologics to facilitate osteogenesis through the implant 12.

In some embodiments, the surgical implant can include, for example, a laterovertically-expanding shell configured to create an intervertebral scaffolding system in vivo, the shell having a first body portion configured to engage a first vertebral endplate and a second body portion configured to engage a second vertebral endplate, the shell further including a collapsed state and an expanded state; a guide element that slideably engages with the distal region of the shell, and is configured for retaining the shell from lateral movement that exceeds the expanded state; and, a shim configured for in vivo introduction into the shell when the shell is in a collapsed state and thereafter causing expansion of the shell to an expanded state, the expansion occurring in a lateral direction and a vertical direction. In some embodiments, the shell is configured to extend asymmetrically in the lateral direction.

One of skill will appreciate that the terms "lateral", "vertical", and "laterovertical" can be used as terms of relative orientation, meaning that the surgical implant can expand in at two directions that are normal to each other. In some embodiments, the term "vertical" can be used herein synonymously with "cephalocaudal", "craniocaudal", and the like, meaning that the implant expands at least substantially in the vertical direction of the spine, at least substantially in the directions of the coronal and sagittal planes of the subject, expanding the intervertebral space by applying a force to the two vertebral endplates that define the upper and lower borders of the intervertebral space. In some embodiments, the term "lateral" can be used herein synonymously with the term "transverse", which encompasses the terms "mediolateral", "anteromedial", "posteromedial", and the like, meaning that the implant expands in any direction that is at least substantially in the direction of a transverse plane of the subject. This can include, for example, expanding the implant toward the annular walls of the disc space, in some embodiments, and away from the annular walls in some embodiments. Likewise, the term "laterovertical" can be used, for example, to refer to an expansion that is at least substantially in the "cephalocaudal" or "craniocaudal" direction combined with an expansion that is at least substantially in the direction of a transverse plane, noting that the transverse plane can be used relative to the subject as a whole, or relative to an anatomical position within the subject, which transverse plane relative to the anatomical position can vary a bit in direction due to normal anatomical variation, or perhaps a disease or disorder.

The term "subject" and "patient" can be used interchangeably in some embodiments and refer to an animal such as a mammal including, but not limited to, non-primates such as, for example, a cow, pig, horse, cat, dog; and primates such as, for example, a monkey or a human. As such, the terms "subject" and "patient" can also be applied to non-human biologic applications including, but not limited to, veterinary, companion animals, commercial livestock, and the like.

The term "at least substantially" will be understood by those of skill in the art as a term that provides for some variance from a strict and narrowly construed direction, essentially meaning "generally in that direction" or "generally in that orientation". This is because, although the orientation of the implant or its movement is intended to be in a particular direction, a pure orientation or direction is often not reasonable to expect in practical application within a subject, and a reasonable amount of deviation in that direction is understood and acceptable by those of skill for the purposes of understanding the scope of, and practicing, the teachings provided herein. In some embodiments, for example, an orientation is at least substantially on a plane or a direction when it's orientation deviates from the plane or direction by no more than 40%, no more than 30%, no more than 20%, no more than 10%, no more than 5%, no more than 1%, or no more than any amount or range therein in increments of 0.1%. In some embodiments, the vertical expansion of the vertebral implant in an intervertebral space can occur, for example, in a direction that is still "craniocaudal" and is understood to be at least substantially parallel to the vertical axis of the intervertebral disc space, for example, such that the vertical axis of the intervertebral disc space is defined by a line connecting the center of the top vertebral endplate and the center of the bottom vertebral endplate defining that intervertebral space when combined with the annulus surrounding the space. Likewise, in some embodiments, the lateral expansion of the vertebral implant in an intervertebral space can occur, for example, in a direction that is at least substantially parallel to any direction of a transverse plane through the intervertebral disc space. In some embodiments, the transverse plane of the intervertebral disc space can be defined by a transverse section of the annulus of the disc rather than a transverse section of the subject, the transverse plane being placed equidistant between the top vertebral endplate and the bottom vertebral endplate, the transverse section of the disc space varying from a transverse section of the subject as a whole, as it is tilted to account for any lordosis, kyphosis, scoliosis, or bone degeneration or disease which can alter the relative position of the intervertebral space within the subject from an otherwise pure interpretation of the orientation intended.

In some embodiments, the biologics delivery system comprises a cannula having a proximal portion, a proximal end, a distal portion, a distal end, and an engagement feature to engage a spinal implant; the proximal portion having a proximal lumen with a first inner diameter, and the distal portion having a distal lumen with a second inner diameter; wherein, the cannula is adapted for receiving a load cartridge in the proximal lumen of the cannula, the load cartridge having a proximal portion, a first removal component, an elongated shaft, and a lumen. Moreover, the cartridge tamp can have an elongated shaft and a second removal component. In such embodiments, the proximal lumen of the cannula can be configured to open into the distal lumen of the cannula, and the lumen of the load cartridge can be configured to open into the distal lumen of the cannula. The proximal lumen of the cannula can be adapted to receive the elongated shaft of the load cartridge, and the distal lumen of the cannula can be adapted to receive the elongated shaft of the load cartridge. In fact, the proximal portion of the load cartridge can be adapted to receive the elongated shaft of the cartridge tamp; and, the second removal component of the cartridge tamp can be adapted to (i) releasably connect with the first removal component and (ii) capture the load cartridge from the cannula when removing the cartridge tamp from the system. In some embodiments, the biologics system can further comprise the load cartridge.

Figure 8:
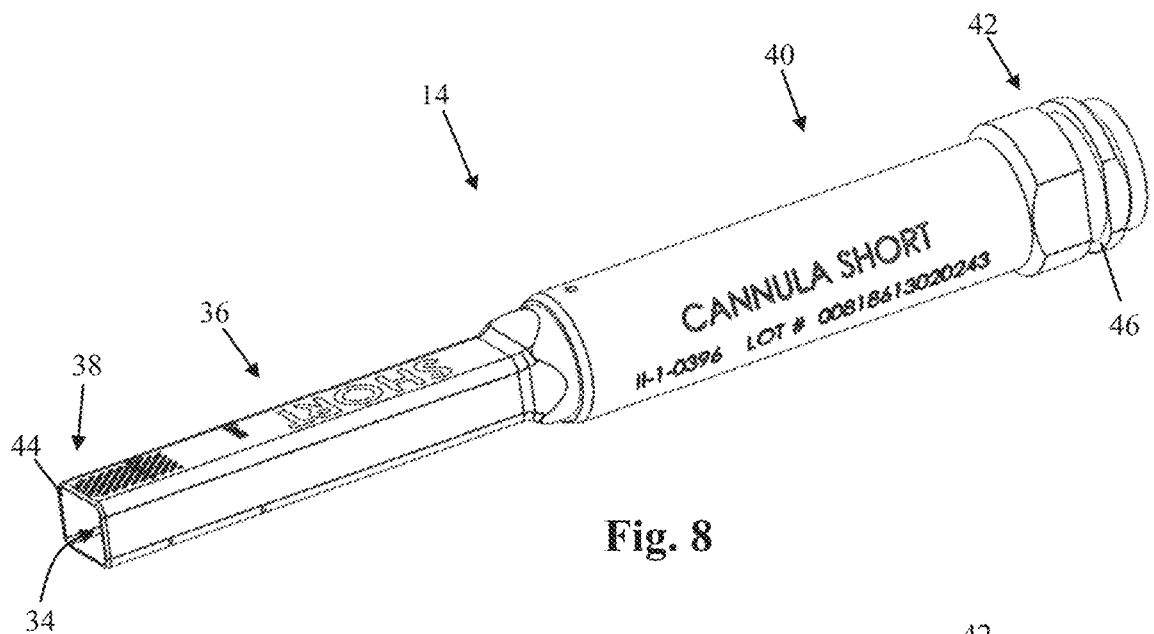
FIG. 8 is a perspective view of one example of an outer cannula forming part of the surgical biologics delivery system of FIG. 1.
Figure 9:
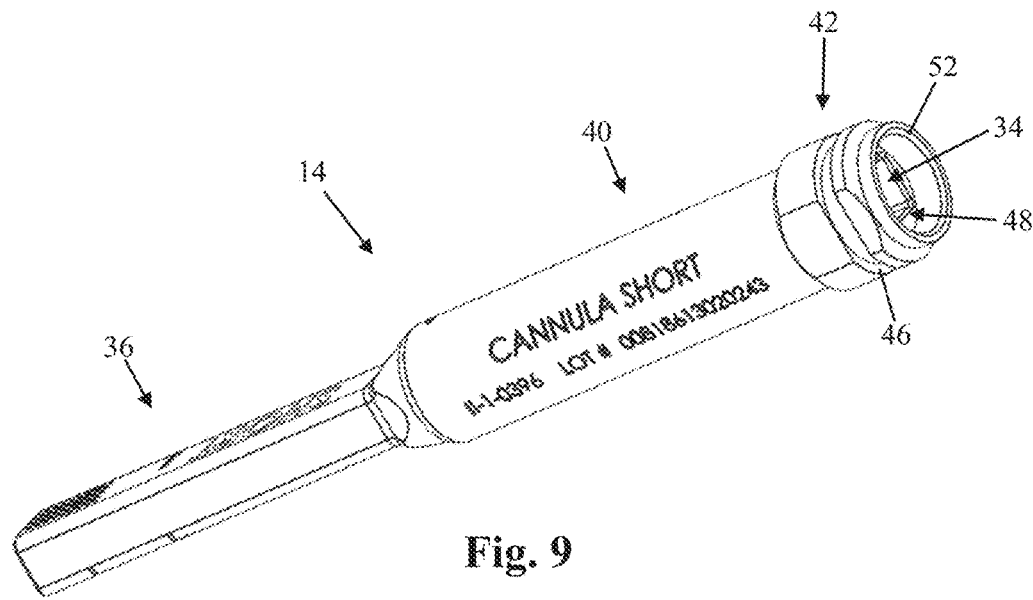
FIG. 9 is another perspective view of the outer cannula of FIG. 8.
Figure 10:
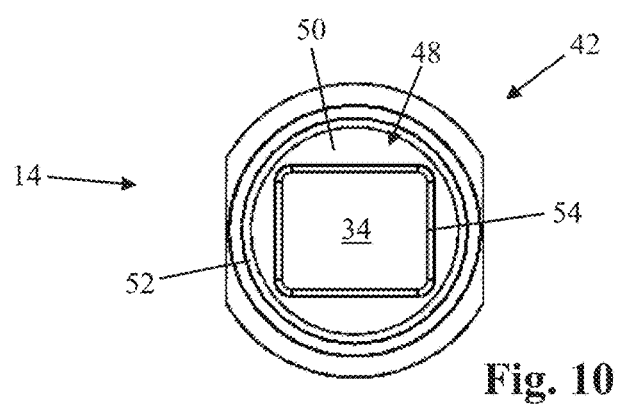
FIG. 10 is a plan view of one end of the outer cannula of FIG. 8.
Figure 11:
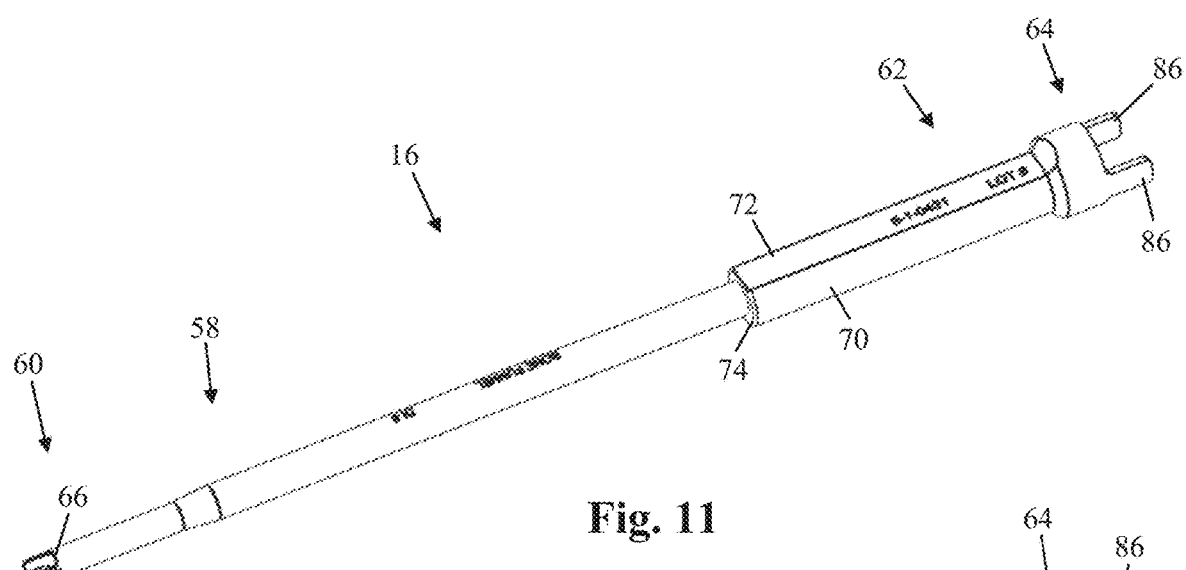
FIG. 11 is a perspective view of an example of an inner cannula forming part of the surgical biologics delivery system of FIG. 1.
Figure 12:
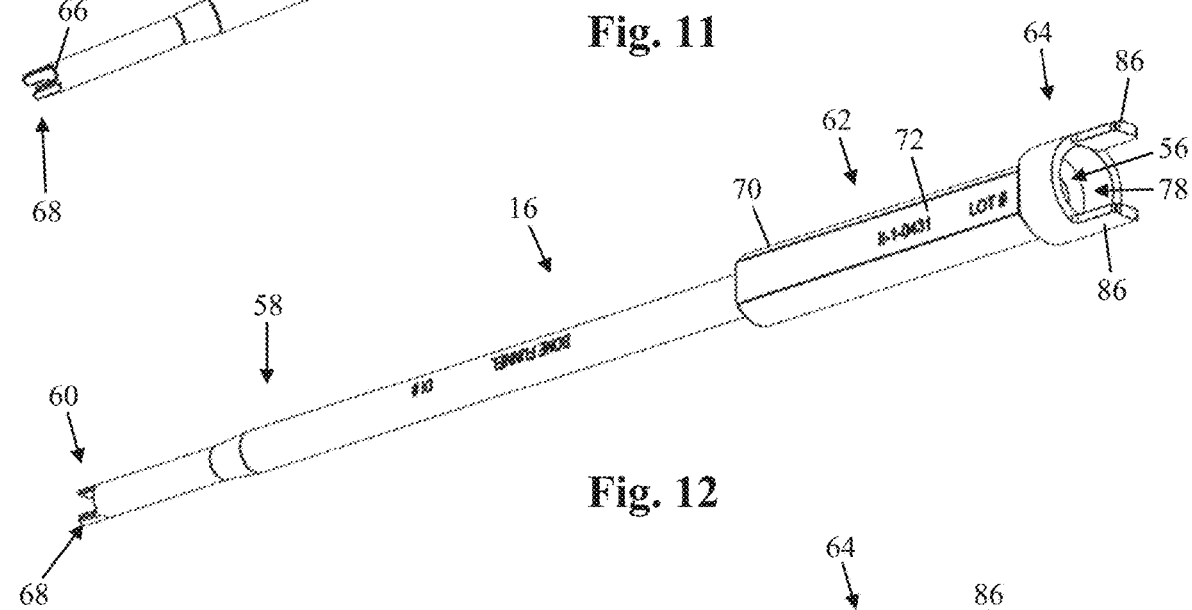
FIG. 12 is another perspective view of the inner cannula of FIG. 11.
Figure 13:
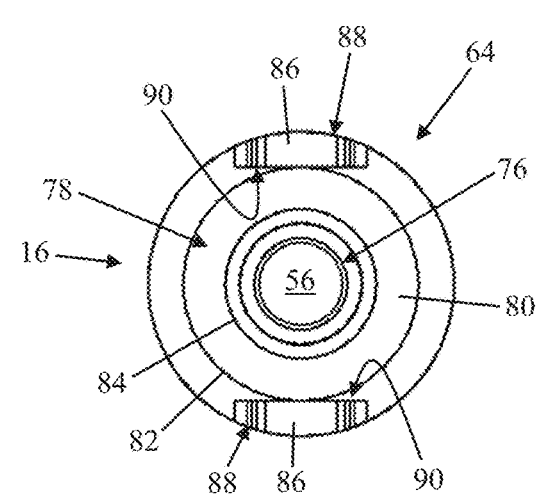
FIG. 13 is a plan view of one end of the inner cannula of FIG. 11.
Figure 14:
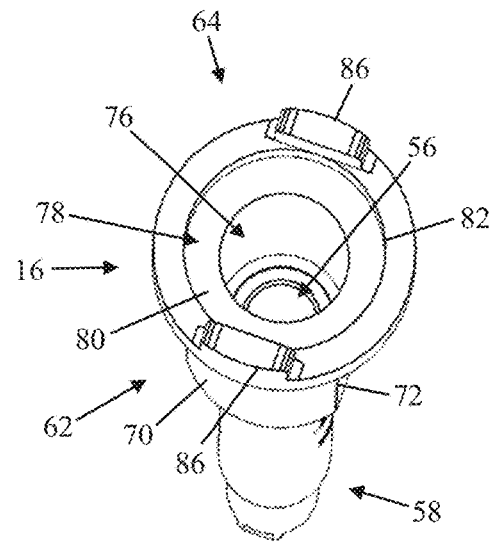
FIG. 14 is a perspective view of one end of the inner cannula of FIG. 11.

FIGS. 8-10 illustrate an example of an outer cannula 14 forming part of the surgical biologics delivery system 10, according to some embodiments. By way of example, the outer cannula 14 comprises an elongated shaft having an interior lumen 34 extending longitudinally therethrough. The elongated shaft further includes a distal portion 36 having a distal end 38 and a proximal portion 40 having a proximal end 42. By way of example, the interior lumen 34 has a generally rectangular cross-sectional shape, as best shown in FIG. 10. The rectangular shape allows for efficient passage of a collapsed spinal implant 12 as well as a shim 24 therethrough. By way of example, the distal portion 36 is configured to extend into a patient's body to the surgical target site, and has a generally rectangular outer peripheral cross-sectional shape to complement the peripheral shape of the interior lumen 34 so as to reduce the profile of the instrument and therefore minimize the impact on nearby body tissue. A distal aperture 44 formed in the distal end 38 provides access to the interior lumen 34.

By way of example, the proximal portion 40 extends away from the patient's body and is generally cylindrical in shape. The proximal end 42 includes an engagement recess 46 extending around the periphery of the proximal end 42 configured to facilitate attachment of additional instrumentation and/or accessories. The proximal end 42 further includes a proximal recess 48 formed longitudinally within the proximal end 42 includes a generally planar bottom surface 50 and a cylindrical sidewall 52 extending proximally away from the bottom surface 50. The bottom surface 50 further includes a proximal aperture 54 formed therethrough to provide access to the interior lumen 34. The proximal recess 48 is sized and configured to receive at least a portion of the proximal portion 62 of the inner cannula 16. As will be explained in further detail below, the bottom surface 50 provides a physical barrier to limit the advancement of the inner cannula 16 within the outer cannula 14 to prevent over-insertion. The sidewall 52 engages the inner cannula 16 to prevent unwanted lateral movement of the inner cannula 16 while allowing for rotational movement of the inner cannula 16 within the outer cannula 14 to ensure proper engagement with the implanted spinal implant 12 before delivery of surgical biologics.

In some embodiments, the proximal end of the cannula, for example inner cannula 16, can be further adapted to include a first indicator; and, likewise, the proximal portion of the load cartridge can be further adapted to include a second indicator complementary to the first indicator. In such embodiments, an assembly of the cannula and load cartridge can releasably fix the rotational position of the first removal component relative to the rotational position of the cannula to stop undesirable rotation between the cannula and load cartridge while holding the cannula in vivo to make the releasable connection between the first removal component and second removal component.

FIGS. 11-14 illustrate an example of an inner cannula 16 forming part of the surgical biologics delivery system 10 according to some embodiments. By way of example, the inner cannula 16 comprises an elongated shaft including a distal portion 58 having a distal end 60 and a proximal portion 62 having a proximal end 64. By way of example, the distal portion 58 is configured to extend through the outer cannula 14 to the surgical target site, and has a generally cylindrical interior lumen 56 extending therethrough. A distal aperture 66 formed in the distal end 60 provides access to the interior lumen 56. The distal end 60 further includes an implant engagement feature 68, shown by way of example as a pair of distally extending prongs. The implant engagement feature 68 is configured to engage the implanted spinal implant 12 to dock the distal end 60 of the inner cannula 16 to the surgical implant 12 prior to delivery of surgical biologics. In the instant example, the implant engagement feature 68 (e.g. prongs) is sized and configured for insertion into the proximal aperture 30 of the shim 24 of the spinal implant 12. The implant engagement feature 68 has a width element (e.g. the distance between the outer edges of each of the prongs) that corresponds to the width dimension of the proximal aperture 30 and a height element (e.g. the height of each of the prongs) that corresponds to the height dimension of the proximal aperture 30. In this manner, the distal end 60 is prevented from both lateral and rotational movement within the proximal aperture 30, resulting in a stable docking interaction between the inner cannula 16 and the implant 12. Any suitable means for docking can be used, such that the docking results in making a releasable contact with the implant in vivo.

The docking means can have any shape, including round, square, rectangular, elliptical, sinusoidal, a combination thereof, and the like, and the docking of course, can include complementary shapes between the cannula and the implant. Such means can include a male/female type connection in some embodiments, for example, a straight tube type connector, a stepped tube type connector, a tapered tube type connector, a funnel type connector, a Luer-lock or Luer-slip type connector, a bayonet type connector, a compression type connector, or a slidably translational connection of any configuration, including prongs, tabs, pins, rods, tubes, etc, in some embodiments. In some embodiments, the connection can be a rotationally releasable tab and slot type connection, for example. Moreover, in some embodiments, a pinch-type or grab-type connection may be used, or perhaps a thread fit connection, or perhaps a clip-type connection, in some embodiments.

The proximal portion 62 includes (by way of example) a pair of opposing arcuate surfaces 70 and a pair of opposing planar surfaces 72. The opposing arcuate surfaces 70 are configured to engage the cylindrical sidewall 52 of the proximal recess 48 of the outer cannula 14 when the inner cannula 16 is inserted into the outer cannula 14. Thus the distance between the opposing arcuate surfaces is approximately equal to the diameter of the proximal recess 48. This creates a flush engagement of the proximal portion 62 of the inner cannula 16 within the proximal recess 48 of the outer cannula 14 which allows for rotational movement (e.g. to ensure proper alignment of the implant engagement feature 68 with the spinal implant 12 as described above) while preventing lateral movement within the proximal recess 48. The proximal portion 62 further includes a distal ledge 74 at the intersection of the distal portion 58 and proximal portion 62, created due to the difference in size between the proximal and distal portions 62, 58, respectively (for example, the generally cylindrical distal portion 58 has a diameter that is smaller than the distance between both the opposing arcuate surfaces 70 and the opposing planar surfaces 72. The distal ledge 74 interacts with the bottom surface 50 of the proximal recess 48 to physically block further advancement of the inner cannula 16 within the outer cannula 14.

The proximal portion 62 further includes a generally cylindrical interior lumen 76 sized and configured to receive the load cartridge 18 therein. The interior lumen 76 is contiguous with the interior lumen 56 of the distal portion 58 and has a diameter that is greater than the diameter of the interior lumen 56 of the distal portion 58.

The proximal end 64 includes a proximal recess 78 formed longitudinally within the proximal end 64 includes a generally planar bottom surface 80 and a cylindrical sidewall 82 extending proximally away from the bottom surface 80. The bottom surface 80 further includes a proximal aperture 84 formed therethrough to provide access to the interior lumen 76. The proximal recess 78 is sized and configured to receive at least a portion of the proximal portion 96 of the load cartridge 18. The bottom surface 80 provides a physical barrier to limit the advancement of the load cartridge 18 within the inner cannula 16. The sidewall 82 engages the load cartridge 18 to securely seat the load cartridge 18 within the proximal recess 78. The proximal end 64 further includes a pair of opposing proximal prongs 86 extending proximally away from the proximal end 64. Each prong 86 includes an outer-facing arcuate surface 88 and an inner-facing planar surface 90. The inner-facing planar surfaces 90 flushly engage the planar portions 118 of the upper outer-facing surface 116 of proximal portion 96 of the load cartridge 18 (described below) to ensure proper alignment and prevent rotation of the load cartridge 18 within the inner cannula 16.

Figure 15:
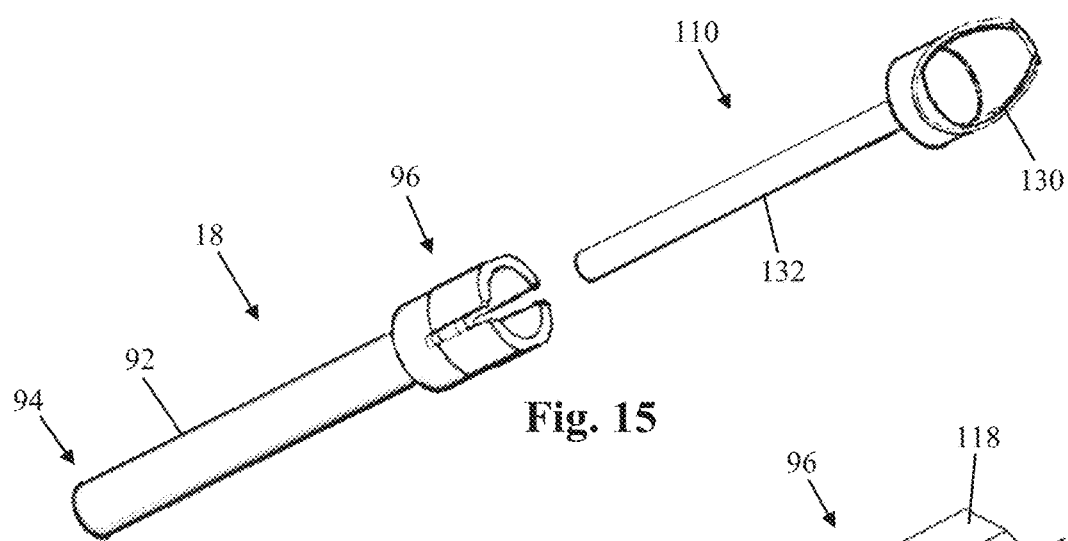
FIG. 15 is a perspective view of an example of a load cartridge and load cartridge tamp forming part of the surgical biologics delivery system of FIG. 1.
Figure 16:
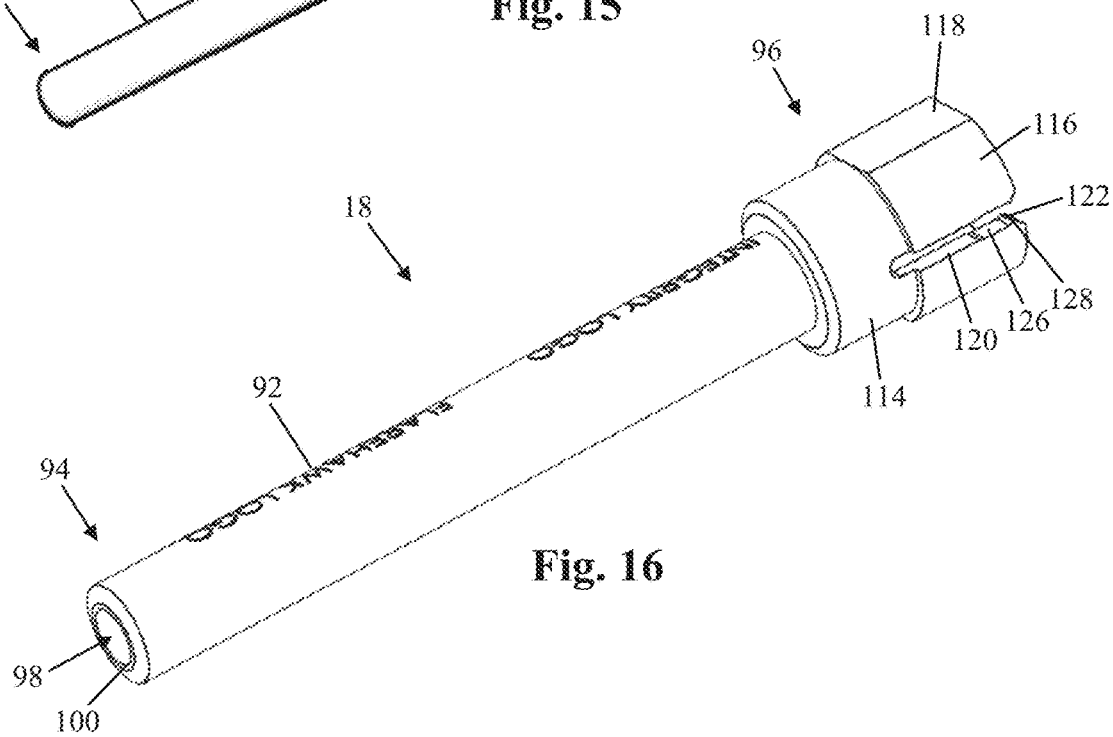
FIG. 16 is a perspective view of the load cartridge of FIG. 15.
Figure 17:
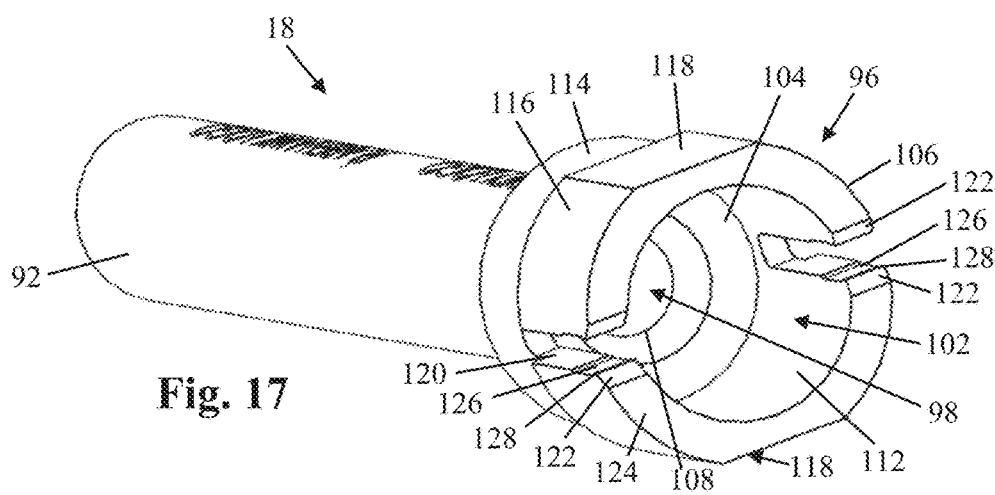
FIG. 17 is another perspective view of the load cartridge of FIG. 15.

FIGS. 15-17 illustrate an example of a load cartridge 18 forming part of the surgical biologics delivery system 10 according to one embodiment of the disclosure. By way of example, the load cartridge 18 comprises a generally cylindrical elongated shaft 92 having a proximal portion 96 and a distal portion 94. The elongated shaft 92 is configured to mate with the proximal portion 62 of the inner cannula 16, and has a generally cylindrical interior lumen 98 extending therethrough. A distal aperture 100 formed in the distal portion 94 provides access to the interior lumen 98.

The proximal portion 96 includes a generally cylindrical proximal recess 102 formed longitudinally within the proximal portion 96 includes a generally planar bottom surface 104 and a cylindrical sidewall 106 extending proximally away from the bottom surface 104. The bottom surface 104 further includes a proximal aperture 108 formed therethrough to provide access to the interior lumen 98. The proximal recess 102 is sized and configured to receive at least a portion of the handle portion 130 of the cartridge tamp 110, which is described in further detail below. The sidewall 106 includes an inner-facing surface 112 having a concave curvature to engage and seat the handle portion 130 of the cartridge tamp 110, a lower outer-facing surface 114 having a convex curvature (e.g. as the outside of a cylinder), and an upper outer-facing surface 116 generally having a convex curvature but also including a pair of planar sections 118 on opposite sides of the sidewall 106. The planar sections 118 are sized and configured to flushly engage the inner-facing planar surfaces 90 of the prongs 86 of the inner cannula 16 when the load cartridge 18 is coupled with the inner cannula 16. This interaction between planar surfaces ensures proper rotational alignment of the load cartridge 18 within the inner cannula 16 for full seating. The lower cylindrical outer-facing surface 114 has a smaller diameter than the upper outer-facing surface 116 such that, upon inserting the load cartridge 18 into the inner cannula 16, the lower outer-facing surface 114 is seated within the proximal recess 78 while the upper outer-facing surface 116 remains outside the proximal recess 78.

The load cartridge removal features are optional, in some embodiments, as the systems and methods have other patentable features, but the load cartridge removal features significantly add to the ease of operation, safety, and reduction in procedural time. It should be appreciated that, in some embodiments, the first removal component can be adapted to releasably engage with the second removal component using a friction fit connection between the first removal component and the second removal component. And, in some embodiments, the first removal component can be adapted to releasably engage with the second removal component using a snap fit connection between the first removal component and the second removal component. And, in some embodiments, the first removal component is adapted to releasably engage with the second removal component using a thread fit connection between the first removal component and the second removal component. In fact, in some embodiments, the first removal component can be adapted to releasably engage with the second removal component using a key and slot coupling connection between the first removal component and the second removal component. It should be further appreciated that, with regard to the systems and methods taught herein that, in some embodiments, the key can be a pin, a bead, or any protuberance known to one of skill in the art, for example; and, the slot can be any configuration that facilitates a releasable capture with the key, including an open slot, a closed slot, an open dimple, a closed dimple, and the like. For example, a slot may be continuous in dimension or tapered for a friction fit, stepped to narrow for a tightening friction fit, stepped to narrow and then wide for a snap fit, and the like or any combination thereof. A thread connection can be any threaded connection and can include a friction fit, for example.

The proximal portion 96 further includes a pair of opposing slots 120 formed longitudinally into the upper outer-facing surface. The slots 120 enable the load cartridge 18 to mate with tamp 20 to allow for easy removal of the load cartridge 18 from the inner cannula 16 after surgical biologics have been delivered to the target site. Each slot 120 includes a pair of chamfers 122 at the intersection between the slot 120 and the proximal face 124 of the proximal portion 96. The chamfers 122 are angled such that they "lead into" the slot 120. Each side of the slot includes a recessed surface 126 positioned distal of the chamfer 122 and a ridge 128 between the chamfer 122 and the recess 126. The space between the recessed surfaces 126 is sized and configured to snugly receive at least a portion of the pin 142 of the tamp 20 (e.g. the distance between the recessed surfaces 126 is approximately equal to the diameter of the pin 142). The distance between the ridges 128 is smaller than the diameter of the pin 142, and therefore the ridges 128 must be laterally displaced to allow the pin 142 to pass by the ridges 128 and reach the recessed area of the slot 120. The length of the slot 120 enables the required lateral displacement. Once the pin 142 passes by the ridges 128, the ridges 128 return to their original position, creating a barrier preventing egress of the pin 142 from the slot 120 and thereby creating a "snap fit" mating between the load cartridge 18 and the tamp 20 (See e.g. FIGS. 22-23). This mating is strong enough to enable simultaneous removal of the load cartridge 18 and tamp 20 from the inner cannula 16 (e.g. removal of the tamp 20 by the user removes the load cartridge 18 as well).

The cartridge tamp 110 includes a handle portion 130 and a pusher 132. The handle may be any structure that enables operability by a user. The pusher 132 is shown by way of example as an elongated cylindrical shaft sized and configured to mate with the interior lumen 98 of the load cartridge 18. The cartridge tamp 110 is used to pack surgical biologic material into the interior lumen 98 of the load cartridge 18 prior to use of the load cartridge 18 in a surgical procedure.

FIGS. 18-21 illustrate an example of a tamp 20 forming part of the surgical biologics delivery system 10, according to some embodiments. The tamp 20 is used to physically relocate surgical biologic material from the load cartridge 18 to the implant 12 within the surgical target site by pushing the material through the inner cannula 16. By way of example, the tamp 20 comprises a generally cylindrical elongated shaft 134 having a distal end 136 and a proximal end 138. The elongated shaft 134 is configured to mate with the interior lumen 56 of the inner cannula 16 and the interior lumen 98 of the load cartridge 18. The distal end 136 is shaped so that the distal end 136 may be at least partially received within the proximal aperture 30 of the implant 12.

In some embodiments, the proximal end of the cartridge tamp can be further adapted to include a third indicator that is complementary to the assembly of the first and second indicators, such that the third indicator guides the cartridge tamp into the releasably-fixed assembly of the cannula and the load cartridge while making the releasable connection in vivo between the first removal component and second removal component. In some embodiments, the first indicator can be configured to include a first prong extending proximally from the proximal end of the cannula and having a flat interior surface; the second indicator, likewise, can be configured with a outer-facing flat surface on the proximal portion of the load cartridge that is at least substantially complementary with the flat interior surface of the first prong; and, the cartridge tamp can further include a proximal cap having a recess as the third indicator, the recess being at least substantially complementary to the first prong.

As further illustrated in FIGS. 18-23, the proximal end 138 includes an end cap 140 and a pin 142. By way of example, the end cap 138 has a generally cylindrical outer surface 144 and a distal recess 146 formed longitudinally within the distal end of the end cap 140. The distal recess 146 includes a generally planar end surface 148 and a cylindrical sidewall 150 extending distally away from the end surface 148. The elongated shaft 134 extends distally from the center of the end surface 148 The distal recess 146 is sized and configured to receive at least a portion of the proximal portion 96 of the load cartridge 18 therein. More specifically, the distal recess 146 is configured to receive the upper outer-facing surface 116 portion of the proximal portion 96 therein. The sidewall 150 includes a pair of opposing longitudinal recesses 152 sized and configured to receive the prongs 86 of the inner cannula 16 therein as the tamp 20 is nearing full insertion (See, e.g. FIGS. 24-26). Seating the prongs 86 within the recesses 152 ensures proper orientation of the distal end 136 of the tamp 20 relative to the distal end 60 of the inner cannula 18 and (perhaps more importantly) the implant 12, and also prevents over-insertion of the tamp 20 in the event that the surgical biologics delivery system 10 is used without the load cartridge 18 (e.g. by loading biologics material directly into the proximal portion 62 of the inner cannula 16). The outer surface 144 further includes a handle element 154 configured to enable efficient handling by a user. By way of example only, the handle element 154 is shown as a friction element (e.g. surface roughening). The pin 142 is generally cylindrical in shape and extends between opposite points on the cylindrical sidewall 150 and through the elongated shaft 134 at a point on the elongated shaft 134 that is vertically displaced from the end surface 148.

Figure 22:
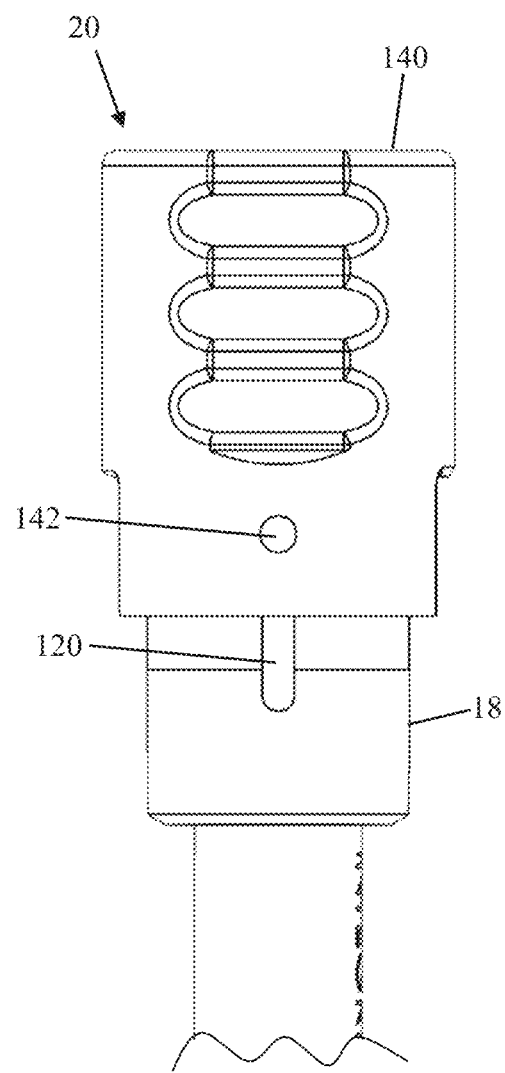
FIG. 22 is an enlarged view of the proximal end engagement between the tamp of FIG. 18 and load cartridge of FIG. 15 according to one embodiment of the disclosure.
Figure 23:
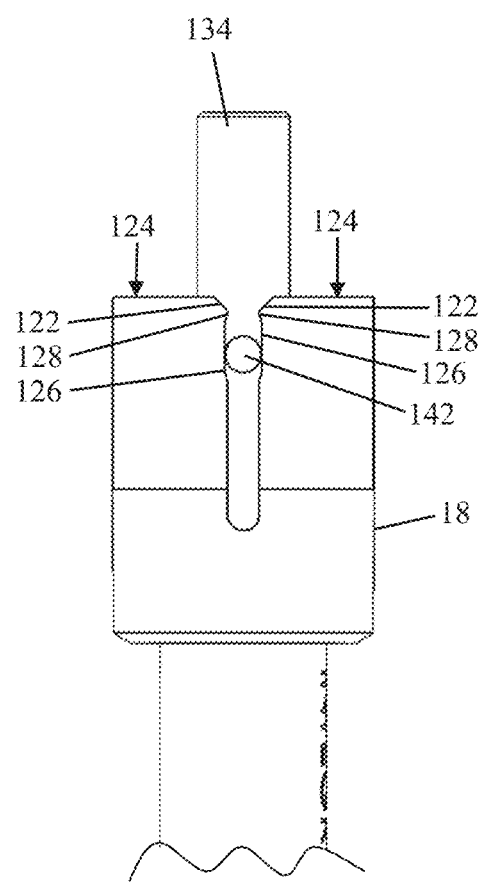
FIG. 23 is an enlarged view of the proximal end engagement between the tamp of FIG. 18 and load cartridge of FIG. 15, with the end cap of the tamp removed.
Figure 24:
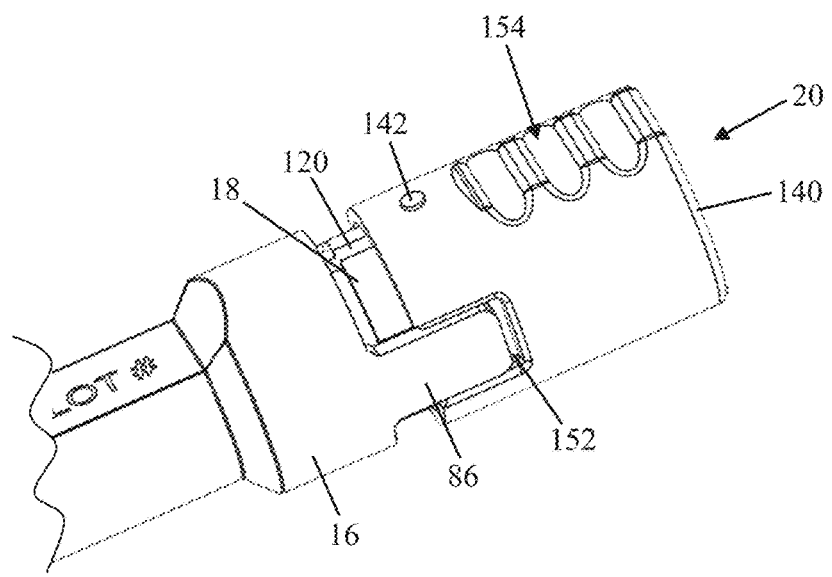
FIG. 24 is an enlarged perspective view of the proximal end engagement between the tamp of FIG. 18, load cartridge of FIG. 15, and inner cannula of FIG. 11 according to one embodiment of the disclosure.
Figure 25:
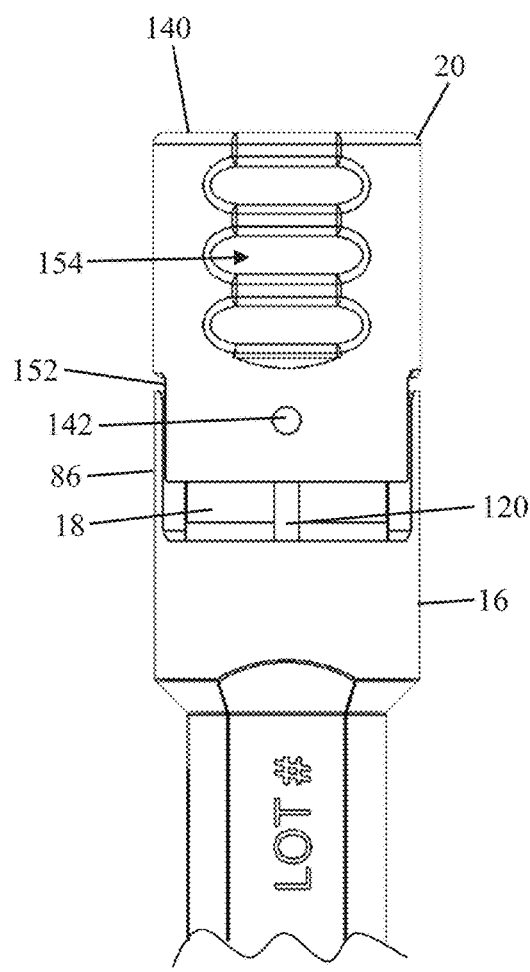
FIG. 25 is an enlarged plan view of the proximal end engagement between the tamp of FIG. 18, load cartridge of FIG. 15, and inner cannula of FIG. 11.
Figure 26:
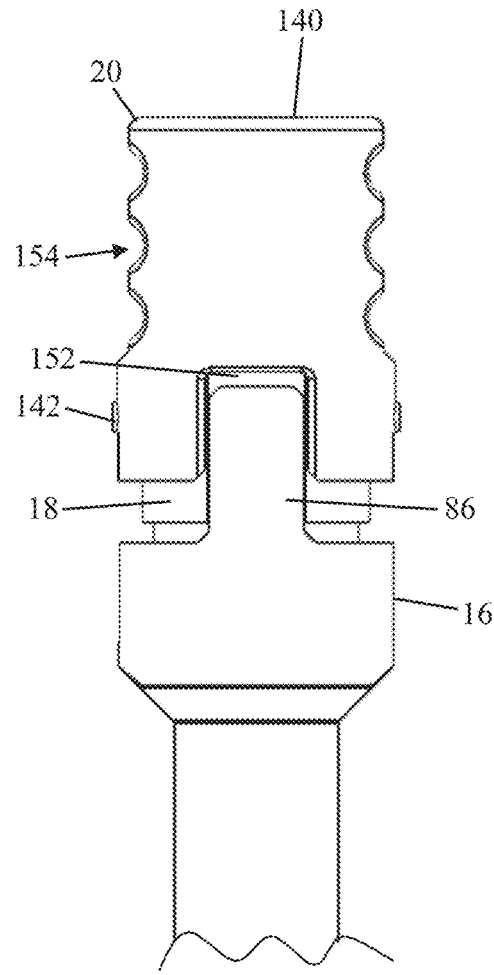
FIG. 26 is another enlarged plan view of the proximal end engagement between the tamp of FIG. 18, load cartridge of FIG. 15, and inner cannula of FIG. 11, rotated 90° relative to the view of FIG. 25.

FIGS. 22-23 illustrate by way of example the interaction between the tamp 20 and load cartridge 18 as described above, according to some embodiments. FIGS. 24-26 illustrate by way of example the interaction between the tamp 20 and the inner cannula 16 as described above, according to some embodiments.

Methods of delivering biologics into an intervertebral disc space of a subject can include a variety of steps. In some embodiments, the methods can include placing a cannula into the intervertebral disc space, the cannula adapted for receiving a preloaded load cartridge, preloaded with fusion promoting material; and, delivering the fusion promoting material by pushing a cartridge tamp into the preloaded cartridge to apply pressure that forces the fusion promoting material into the intervertebral disc space.

In some embodiments, the methods can include placing the cannula into the intervertebral disc space; inserting the load cartridge into the cannula, the load cartridge preloaded with fusion promoting material; and, delivering the fusion promoting material into the intervertebral disc space. In such embodiments, the delivering can include inserting the cartridge tamp into the load cartridge and pushing the fusion promoting material into the intervertebral disc space with the cartridge tamp to create a first empty load cartridge; removing the first empty load cartridge; inserting an additional load cartridge into the cannula, the additional load cartridge preloaded with additional fusion promoting material; pushing the additional fusion promoting material into the intervertebral disc space with the cartridge tamp to create an additional empty load cartridge; removing the additional empty load cartridge; and, repeating inserting the additional load cartridge, pushing the additional load cartridge, and removing the additional load cartridge until a desired amount of fusion promoting material has been delivered to the intervertebral space. In some embodiments, the load cartridges are administered in series, where the first cartridge is "load cartridge 1", and each additional load cartridges, n, is an "n+1"$^{th}$ load cartridge, for example, where n can range from, perhaps, from 1 to 10.

In some embodiments, the methods can further comprise inserting a spinal implant into the intervertebral disc space. And, in some embodiments, the methods can further comprise docking the distal end of the cannula to the spinal implant. The insertion of the spinal implant can be done using a first cannula, which can be referred to as an outer cannula in some embodiments. This first cannula, however, can either be removed for a subsequent insertion of the cannulas taught herein for receiving the load cartridges, or it can remain in place during the biologics delivery procedure as the "outer cannula", such that it is large enough to accept an insertion of the cannulas taught herein for receiving the load cartridges.

Moreover, in some embodiments, the removing of the first load cartridge and the additional load cartridge can include releasably engaging the first removal component with the second removal component using a friction fit connection between the first removal component and the second removal component. And, in some embodiments, the removing of the first load cartridge and the additional load cartridge can include releasably engaging the first removal component with the second removal component using a snap fit connection between the first removal component and the second removal component. And, in some embodiments, the removing of the first load cartridge and the additional load cartridge can include releasably engaging the first removal component with the second removal component using a thread fit connection between the first removal component and the second removal component. And, in some embodiments, the removing of the first load cartridge and the additional load cartridge can include releasably engaging the first removal component with the second removal component using a key and slot coupling connection between the first removal component and the second removal component. It should be appreciated that any releasably engaging means known to those of skill can be used, such that the cartridge tamp can releasably capture and remove a spent load cartridge. It should be appreciated, for example that such a means for releasably capturing a spent load cartridge may include, for example, a connection of any configuration, including prongs, tabs, pins, rods, tubes, etc, in some embodiments, that can slidably or rotational capture and release a load cartridge from the cannula. In some embodiments, the connection can be a rotationally releasable tab and slot type connection, or perhaps a peg/pin and slot type connection, for example. Moreover, in some embodiments, a pinch-type or grab-type connection may be used, or perhaps a thread fit connection, or perhaps even a clip-type connection, in some embodiments, as a means for releasably capturing the spent load cartridge.

In some embodiments, the methods further include inserting an expandable shell into the intervertebral disc space. In some embodiments, the methods further include inserting a shim into the intervertebral disc space. In some embodiments, the methods further include inserting an expandable shell into the intervertebral disc space and inserting a shim into the expandable shell. And, in some embodiments, the methods further include expanding the expandable shell lateroveritcally.

Figure 27:
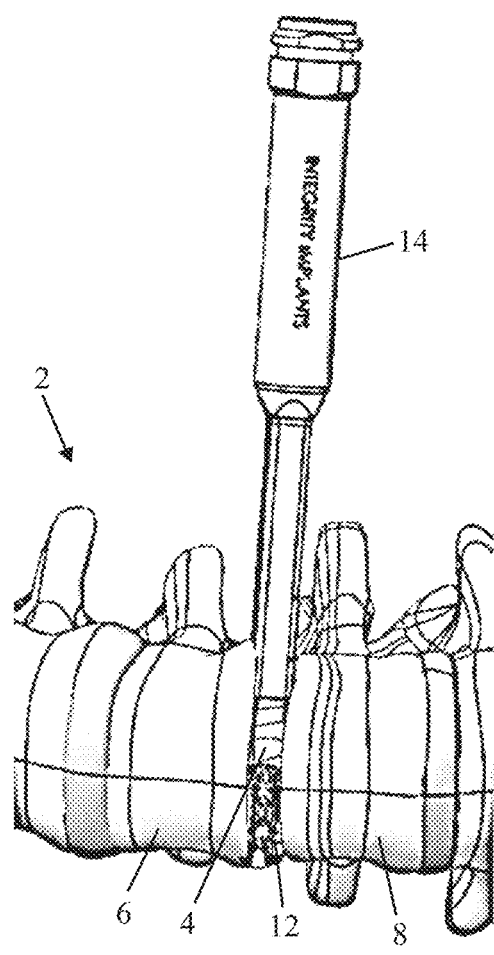
FIG. 27 is a perspective view of one step of an example method of using the surgical biologics delivery system of FIG. 1 according to one embodiment of the disclosure, comprising a step of introducing a spinal implant of FIG. 5 into a target disc space by way of the outer cannula of FIG. 8.
Figure 28:
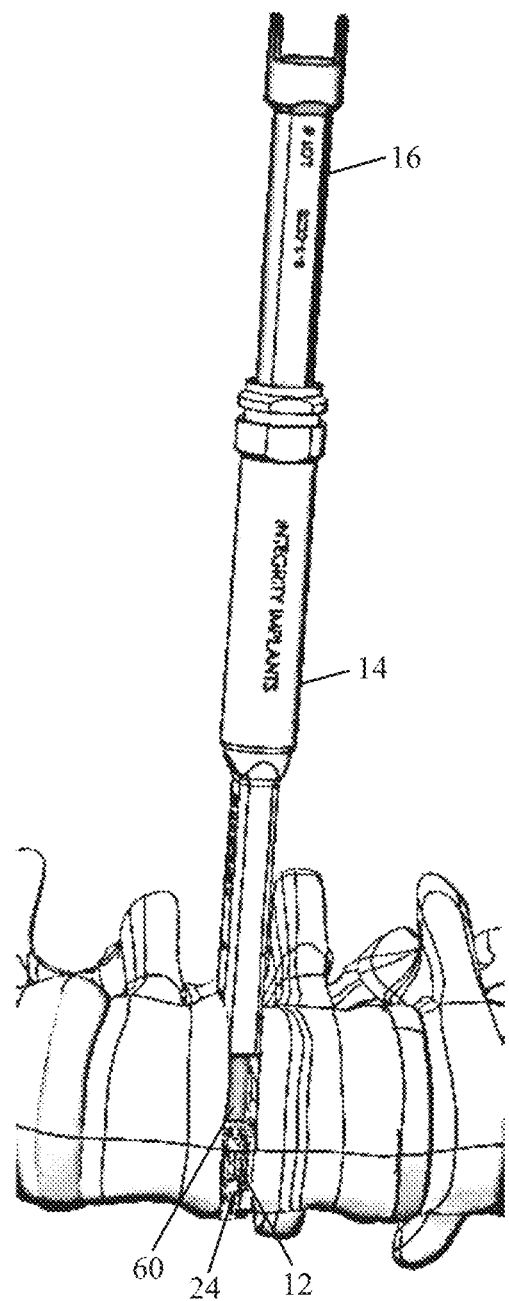
FIG. 28 is a perspective view of another step of an example method of using the surgical biologics delivery system of FIG. 1 according to one embodiment of the disclosure, comprising a step of inserting the inner cannula of FIG. 11 into the outer cannula of FIG. 8.

FIGS. 27-32 illustrate various steps in a example method of using the surgical biologics delivery system 10 of the present disclosure, according to some embodiments. FIG. 27 illustrates a portion of a spinal column 2, including a surgical target comprising an intervertebral disc space 4 located between adjacent vertebrae 6, 8. In the instant example, the disc space 4 has already been prepared (e.g. damaged disc removed, endplates prepared for implant, etc.) and a spinal implant 12 has been inserted into the disc space 4 through the outer cannula 14. As can been seen, the distal portion 36 of the outer cannula 14 is sized to facilitate partial insertion into the disc space. With the outer cannula 14 left in place, the next step is to insert the inner cannula 16 into the outer cannula 14 such that the distal end 60 of the inner cannula 16 engages with the proximal aperture 30 of the shim 24 of the spinal implant 12, as shown by way of example in FIG. 28. As illustrated by way of example in FIG. 29, the next step is to insert a load cartridge 18 into the proximal portion 62 of the inner cannula 16. Preferably, the load cartridge 18 has been preloaded with surgical biologics material prior to insertion in to the inner cannula 16, however the step of loading the load cartridge 18 with biologics may be performed after the load cartridge 18 has been inserted into the inner cannula 16. Alternatively, biologics material may be inserted directly into the inner cannula 16 without the use of the load cartridge 18, if desired. As shown by way of example in FIG. 30, the next step is to insert the elongated shaft 134 of the tamp into the load cartridge 18 and apply a distal force to physically move the surgical biologics material from the load cartridge 18 through the inner cannula 16 and into the spinal implant 12 and intervertebral disc space 4, where it will interact with the vertebral endplates to generate new bone growth through the implant 12 and across the disc space 4.

The load cartridges can be referred to as "repeater" cartridges, in some embodiments, as they are designed for rapid use and replacement during a surgical procedure, and provide surprising results in advancements of procedural speed, ease of operation, and safety. In some embodiments, a replacement of the load cartridge occurs from the time the cartridge becomes empty and is replaced with a fresh cartridge. The replacement time can range from 5 seconds to 60 seconds, from 10 seconds to 45 seconds, from 20 seconds to 30 seconds, or any range therein in increments of 1 second. In some embodiments, the replacement time of a load cartridge can be about 5 seconds, 10 seconds, 15 seconds, 20 seconds, 25 seconds, 30 seconds, 35 seconds, 40 seconds, 45 seconds, 50 seconds, 55 seconds, 60 seconds, or any amount therein in increments of 1 second. Likewise, as with the load cartridges, the "bore" or lumen of the cannula used to receive the load cartridge and deliver the fusion promoting material is large to facilitate a fast delivery into the intervertebral space. Although the bore size can range from about 1.0 mm to about 10.0 mm in diameter, for example, the bore is no less than 5.0 mm in diameter in some embodiments, and any range therein in increments of 1.0 mm. In some embodiments, however, the bore size can range from about 5.0 mm to about 10.0 mm in diameter, or from about 5.0 mm to about 6.0 mm in diameter, and any range therein in increments of 1.0 mm. In some embodiments, the bore size can be no less in diameter than about 5.0 mm, about 6.0 mm, about 7.0 mm, about 8.0 mm, about 9.0 mm, about 10.0 mm, and any amount therein in increments of 1.0 mm. In some embodiments, the bore size can be asymmetrical in dimensions, such that the height of the bore may not be equal to the width of the bore. For example, in some embodiments, the bore size ranges from 5.0 mm to 6.00 mm in height, and from 9.0 mm to 16.00 mm in width. And in some embodiments, the bore size ranges from 5.0 mm to 15.00 mm in height, and from about 9.0-15.0 mm in width. In some embodiments, "height" is a term that can refer to the craniocaudal direction of the bore, and "width" is a term that can refer to the transverse direction with respect to the anatomical position of the subject.

Figure 31:
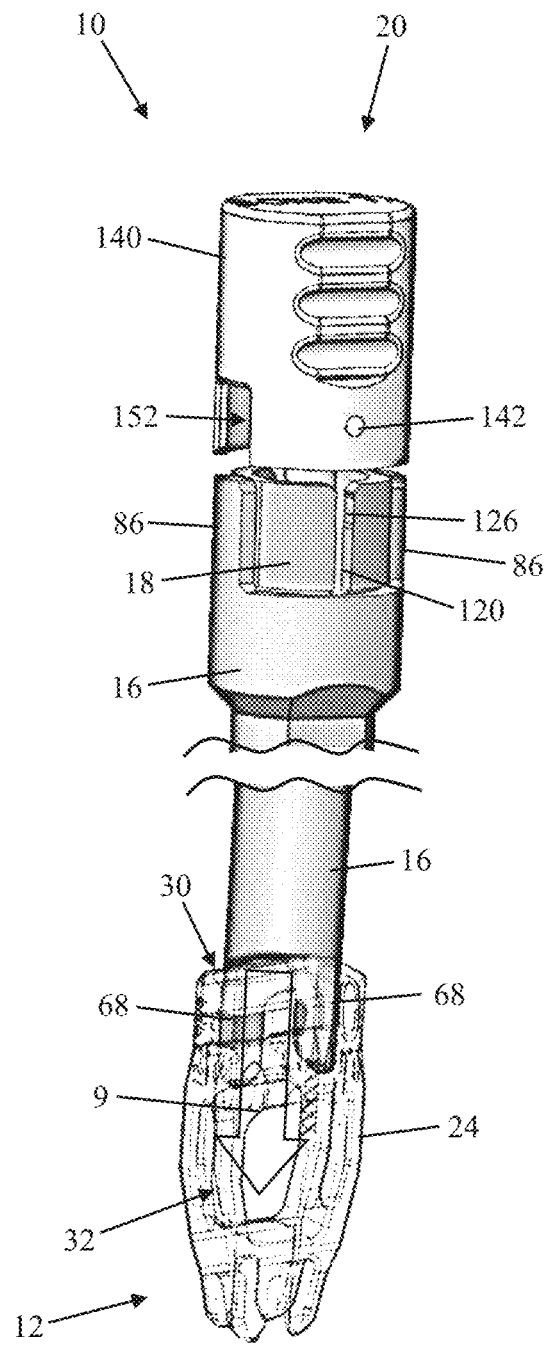
FIG. 31 is a perspective view of the proximal and distal engagements between the tamp of FIG. 18, load cartridge of FIG. 15, and inner cannula of FIG. 11, with the tamp partially inserted.

FIG. 31 illustrates the relative positioning of the various components of the surgical biologics delivery system 10 just prior to final advancement of the tamp 20 into the load cartridge 18 and inner cannula 16, according to some embodiments. For the purpose of illustration, the spinal implant 12 is represented by the shim 24 (e.g. the expandable shell 22 has been omitted), which is shown in transparent form, and the outer cannula 14 is omitted. At this point in the method, the inner cannula 16 is docked to the shim 24 by virtue of the implant engagement feature 68 (e.g. distal prongs) being inserted into the proximal aperture 30 of the shim 24. If the tamp 20 has been advanced far enough, surgical biologics material 9 may begin to egress from the inner cannula 16 into the implant 12. At the proximal end of the assembly, the load cartridge 18 is inserted into the inner cannula 16 and is in proper alignment due to the prongs 86. The end cap 140 of the tamp 20 is positioned such that the sidewall recesses 152 are aligned with the prongs 86 of the inner cannula 16 and the pin 142 is aligned with the slot 120.

Figure 32:
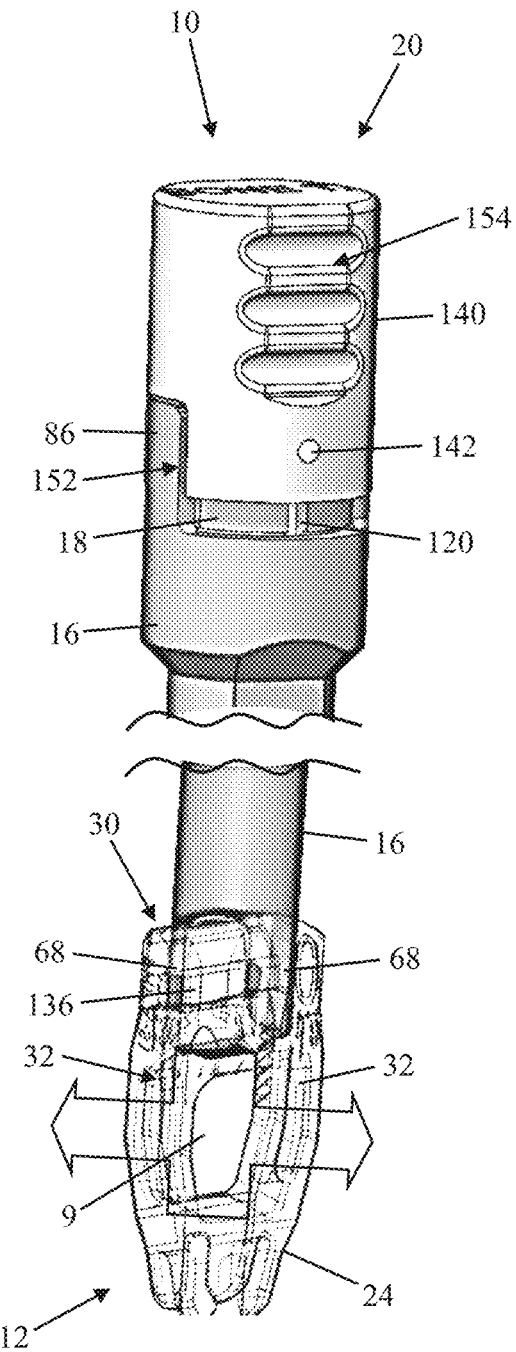
FIG. 32 is a perspective view of the proximal and distal engagements between the tamp of FIG. 18, load cartridge of FIG. 15, and inner cannula of FIG. 11, with the tamp fully inserted.

FIG. 32 illustrates the relative positioning of the various components of the surgical biologics delivery system 10 after final advancement of the tamp 20 into the load cartridge 18 and inner cannula 16, according to some embodiments. Upon final advancement of the tamp 20, the pin 142 will advance into the slot 120 until it snaps into the recessed region 126 of the slot 120. The prongs 86 of the inner cannula 16 are fully inserted into the sidewall recesses 152 of the end cap 140 of the tamp 20, ensuring proper alignment of the tamp 20 and also preventing further insertion of the tamp 20 in the event that a load cartridge 18 is not used. At the distal end of the assembly, the distal end 136 of the elongated shaft 134 is inserted into the implant 12 by way of aperture 30. The biologics material 9 has been fully deposited into the implant 12 and fills the disc space 4 by way of egress through graft windows 32 in the shim 24 and similar graft windows 28 in the expandable shell (not shown).

Once the biologics material 9 has been fully deposited into the implant 12, the user may remove the tamp 20 by gripping the handle element 154 and exerting a proximal force to pull the tamp 20 out of the inner cannula 16. By virtue of the snap-fit coupling engagement between the tamp 20 and load cartridge 18 (by way of the pin 142 and slot 120), the load cartridge 18 is removed from the inner cannula 16 with the tamp 20. The inner cannula 16 may then be removed from the target site by exerting a proximal force on the inner cannula 16 to disengage from the implant 12 and remove the inner cannula 16 from the outer cannula 14. The outer cannula 12 my then be removed in a similar fashion, and the surgical wound may then be closed.

We claim:

1. A biologics delivery system, comprising:
a cannula having a proximal portion, a proximal end, a distal portion, a distal end, and an engagement feature to engage a spinal implant; the proximal portion having a proximal lumen with a first inner diameter, and the distal portion having a distal lumen with a second inner diameter; wherein, the cannula is adapted for receiving a load cartridge in the proximal lumen of the cannula, the load cartridge having a proximal portion, a first removal component, an elongated shaft, and a lumen; and,
a cartridge tamp having an elongated shaft and a second removal component;
wherein,
the proximal lumen of the cannula opens into the distal lumen of the cannula, and the lumen of the load cartridge opens into the distal lumen of the cannula;
the proximal lumen of the cannula is adapted to receive the elongated shaft of the load cartridge, and the distal lumen of the cannula is adapted to receive the elongated shaft of the load cartridge;
the proximal portion of the load cartridge is adapted to receive the elongated shaft of the cartridge tamp; and,
the second removal component of the cartridge tamp is adapted to (i) releasably connect with the first removal component and (ii) capture the load cartridge from the cannula when removing the cartridge tamp from the system.

2. The biologics delivery system of claim 1, further comprising the load cartridge.

3. The biologics delivery system of claim 1, wherein the first removal component is adapted to releasably engage with the second removal component using a friction fit connection between the first removal component and the second removal component.

4. The biologics delivery system of claim 1, wherein the first removal component is adapted to releasably engage with the second removal component using a snap fit connection between the first removal component and the second removal component.

5. The biologics delivery system of claim 1, wherein the first removal component is adapted to releasably engage with the second removal component using a thread fit connection between the first removal component and the second removal component.

6. The biologics delivery system of claim 1, wherein the first removal component is adapted to releasably engage with the second removal component using a key and slot coupling connection between the first removal component and the second removal component.

7. The biologics delivery system of claim 1, wherein
the proximal end of the cannula is further adapted to include a first indicator; and,
the proximal portion of the load cartridge is further adapted to include a second indicator complementary to the first indicator;
wherein, an assembly of the cannula and load cartridge releasably fixes a rotational position of the first removal component relative to a rotational position of the cannula to stop undesirable rotation between the cannula and load cartridge while holding the cannula to make the releasable connection between the first removal component and second removal component in vivo.

8. The biologics delivery system of claim 7, wherein a proximal end of the cartridge tamp is further adapted to include a third indicator that is complementary to the assembly of the first and second indicators, such that the third indicator guides the cartridge tamp into the releasably-fixed assembly of the cannula and the load cartridge while making the releasable connection between the first removal component and second removal component in vivo.

9. The biologics delivery system of claim 8, wherein first indicator includes a first prong extending proximally from the proximal end of the cannula and having a flat interior surface; the second indicator is an outer-facing flat surface on the proximal portion of the load cartridge that is complementary with the flat interior surface of the first prong; and, the cartridge tamp further includes a proximal cap having a recess as the third indicator, the recess being complementary to the first prong.

10. A method of delivering biologics into an intervertebral disc space of a subject using the system of claim 1, the method comprising:
placing the cannula into the intervertebral disc space;
inserting a load cartridge into the cannula, the load cartridge preloaded with fusion promoting material; and,
delivering the fusion promoting material into the intervertebral disc space, the delivering including
inserting the cartridge tamp into the load cartridge and pushing the fusion promoting material into the intervertebral disc space with the cartridge tamp to create a first empty load cartridge;
removing the first empty load cartridge;
inserting an additional load cartridge into the cannula, the additional load cartridge preloaded with additional fusion promoting material;
pushing the additional fusion promoting material into the intervertebral disc space with the cartridge tamp to create an additional empty load cartridge;
removing the additional empty load cartridge; and,
repeating inserting the additional load cartridge, pushing the additional load cartridge, and removing the additional load cartridge until a desired amount of fusion promoting material has been delivered to the intervertebral space.

11. The method of claim 10, further comprising inserting a spinal implant into the intervertebral disc space.

12. The method of claim 11, further comprising docking the distal end of the cannula to the spinal implant.

13. The method of claim 10, wherein the removing of the first empty load cartridge and the additional empty load cartridge includes releasably engaging the first removal component with the second removal component using a friction fit connection between the first removal component and the second removal component.

14. The method of claim 10, wherein the removing of the first empty load cartridge and the additional empty load cartridge includes releasably engaging the first removal component with the second removal component using a snap fit connection between the first removal component and the second removal component.

15. The method of claim 10, wherein the removing of the first empty load cartridge and the additional empty load cartridge includes releasably engaging the first removal component with the second removal component using a thread fit connection between the first removal component and the second removal component.

16. The method of claim 10, wherein the removing of the first empty load cartridge and the additional empty load cartridge includes releasably engaging the first removal component with the second removal component using a key and slot coupling connection between the first removal component and the second removal component.

17. The method of claim 10, further comprising inserting an expandable shell into the intervertebral disc space.

18. The method of claim 17, further comprising expanding the expandable shell laterovertically.

19. The method of claim 10, further comprising inserting a shim into the intervertebral disc space.

20. The method of claim 10, further comprising inserting an expandable shell into the intervertebral disc space and inserting a shim into the expandable shell.

* * * * *